(12) United States Patent
Kim et al.

(10) Patent No.: US 12,138,283 B2
(45) Date of Patent: Nov. 12, 2024

(54) METHOD OF PREPARING THREE-DIMENSIONAL CELL SPHEROID INCLUDING ADIPOSE-DERIVED STEM CELLS AND HEPATOCYTES

(71) Applicant: KOREA INSTITUTE OF SCIENCE AND TECHNOLOGY, Seoul (KR)

(72) Inventors: Sang-Heon Kim, Seoul (KR); Seokheon Hong, Seoul (KR); Seung Ja Oh, Seoul (KR); Kwi Deok Park, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 804 days.

(21) Appl. No.: 16/413,278

(22) Filed: May 15, 2019

(65) Prior Publication Data
US 2019/0374580 A1    Dec. 12, 2019

(30) Foreign Application Priority Data
May 17, 2018 (KR) .................. 10-2018-0056768

(51) Int. Cl.
| | | |
|---|---|---|
| *A61K 35/28* | (2015.01) | |
| *A61K 9/16* | (2006.01) | |
| *C12N 5/0775* | (2010.01) | |

(52) U.S. Cl.
CPC ............. *A61K 35/28* (2013.01); *A61K 9/16* (2013.01); *C12N 5/0667* (2013.01); *C12N 2501/105* (2013.01); *C12N 2501/11* (2013.01); *C12N 2501/113* (2013.01); *C12N 2501/115* (2013.01); *C12N 2501/12* (2013.01); *C12N 2501/135* (2013.01); *C12N 2501/165* (2013.01); *C12N 2502/1382* (2013.01); *C12N 2502/14* (2013.01); *C12N 2513/00* (2013.01)

(58) Field of Classification Search
CPC ........ A61K 35/28; A61K 9/16; C12N 5/0667; C12N 2501/105; C12N 2501/11; C12N 2501/113; C12N 2501/115; C12N 2501/12; C12N 2501/135; C12N 2501/165; C12N 2502/1382; C12N 2502/14; C12N 2513/00
See application file for complete search history.

(56) References Cited

U.S. PATENT DOCUMENTS

2012/0122156 A1    5/2012    Kim et al.

FOREIGN PATENT DOCUMENTS

| KR | 1020100122778 A | * 10/2010 | ............. C12N 5/071 |
|---|---|---|---|
| KR | 10-2014-0113139 A | 9/2014 | |

OTHER PUBLICATIONS

Zhang, et al., Spheroid formation and differentiation into hepatocyte-like cells of rat mesenchymal stem cell induced by co-culture with liver cells, DNA and Cell Biology, 26(7): 497-503. (Year: 2007).*
Alzebdeh et al., Metabolic oscillations in co-cultures of hepatocytes and mesenchymal stem cells: effects of seeding arrangement and culture mixing, Journal of Cellular Biochemistry, 118: 3003-3015. (Year: 2017).*
Park et al., A novel three-dimensional adipose-derived stem cell cluster for vascular regeneration in ischemic tissue, Cytotherapy, 16: 508-522. (Year: 2014).*
Zhang Weitao, Efficient generation of functional hepatocyte-like cells from human fetal hepatic progenitor cells in vitro, Journal of Cellular Physiology, p. 2051-2058. (Year: 2011).*
Southern Labware, 6 well culture plate, retrieved from internet Aug. 10, 2022. (Year: 2022).*
Yahoo et al., Forced expression of Hnf1b/Foxa3 promotes hepatic fate of embryonic stem cells, Biochemical and Biophysical Research Communications, 475: 199-205. (Year: 2016).*
Kim et al., KR20100122778A1, Fibroblasts growth factor recombinant protein with adhesive activity to stem cells and method of culturing stem cells using the same, machine translation. (Year: 2010).*
Kobayashi et al., Receptor-mediated regulation of differentiation and proliferation of hepatocytes by synthetic polymer model of asialoglycoprotein, J Biomater Sci Polymer Edn, 6(4): 325-342. (Year: 1994).*
Al Battah et al., Current Status of Human Adipose-Derived Stem Cells: Differentiation into Hepatocyte-Like Cells, The Scientific World Journal, 11: 156-1581. (Year: 2011).*
Taléns-Visconti et al., Hepatogenic differentiation of human mesenchymal stem cells from adipose tissue in comparison with bone marrow mesenchymal stem cells, World Journal of Gastroenterology, 12(36): 5834-5845. (Year: 2006).*

(Continued)

*Primary Examiner* — Arthur S Leonard
*Assistant Examiner* — Joseph Paul Miano
(74) *Attorney, Agent, or Firm* — Birch, Stewart, Kolasch & Birch, LLP

(57) ABSTRACT

Provided is a method of preparing a three-dimensional cell spheroid, the method including forming the cell spheroid by co-culturing adipose-derived stem cells or mesenchymal stem cells with hepatocytes. According to the cell spheroid prepared by the method, the secretome secreted by the adipose-derived stem cells affects hepatocyte maturation, and therefore, hepatic functions of the finally formed three-dimensional cell spheroid, i.e., organoid, may be enhanced. Further, a composition including a culture medium of the adipose-derived stem cells may prevent or treat liver diseases including hepatitis, hepatotoxicity, cholestasis, fatty liver, etc., and may enhance hepatic functions.

12 Claims, 18 Drawing Sheets

Specification includes a Sequence Listing.

(56) References Cited

OTHER PUBLICATIONS

No et al., "Functional 3D Human Primary Hepatocyte Spheroids Made by Co-Culturing Hepatocytes from Partial Hepatectomy Specimens and Human Adipose-Derived Stem Cells"., PLOS ONE, vol. 7, Issue 12, e50723, Dec. 2012, 8 pages.
Office Action for KR 10-2018-0056768 dated Apr. 16, 2019.
TERMIS Americas 2017 Annual Conference & Exhibition dated Dec. 4, 2017, 13 Pages.
Kang et al., "Control of mesenchymal stem cell phenotype and differentiation depending on cell adhesion mechanism," European Cells and Materials, vol. 28, 2014, pp. 387-403.
Korean Decision of Rejection for Korean Application No. 10-2018-0056768, dated Jan. 9, 2020.
Office Action issued Oct. 26, 2020, in Republic of Korea Patent Application No. 10-2020-0019168.

\* cited by examiner

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic primer: HNF4a

<400> SEQUENCE: 1
atcgtcaagc ctccctctgc                                              20

<210> SEQ ID NO 2
<211> LENGTH: 22
```

```
<212> TYPE: DNA
<213> ORGANISM: Artificial Sequence
<220> FEATURE:
<223> OTHER INFORMATION: Synthetic primer: HNF4a

<400> SEQUENCE: 2
gactggtccc tcgtgtcaca tc                                            22

<210> SEQ ID NO 3
<211> LENGTH: 20
<212> TYPE: DNA
<213> ORGANISM: Artificial Sequence
<220> FEATURE:
<223> OTHER INFORMATION: Synthetic primer: CYP1a2

<400> SEQUENCE: 3
aggagctgga cacggtggtt                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer: CYP1a2

<400> SEQUENCE: 4
aggtgtccct cgttgtgctg                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer: ALB

<400> SEQUENCE: 5
ggctacagcg gagcaactga                                               20

<210> SEQ ID NO 6
<211> LENGTH: 22
<212> TYPE: DNA
<213> ORGANISM: Artificial Sequence
<220> FEATURE:
<223> OTHER INFORMATION: Synthetic primer: ALB

<400> SEQUENCE: 6
gcctgagaag gttgtggttg tg                                            22

<210> SEQ ID NO 7
<211> LENGTH: 25
<212> TYPE: DNA
<213> ORGANISM: Artificial Sequence
<220> FEATURE:
<223> OTHER INFORMATION: Synthetic primer: ASGR1

<400> SEQUENCE: 7
ggtgacctcc agggatgagc agaac                                         25

<210> SEQ ID NO 8
<211> LENGTH: 26
<212> TYPE: DNA
<213> ORGANISM: Artificial Sequence
```

```
<220> FEATURE:
<223> OTHER INFORMATION: Synthetic primer: ASGR1

<400> SEQUENCE: 8
ctgttccatc cacccatttc cagggc                                                26
```

METHOD OF PREPARING THREE-DIMENSIONAL CELL SPHEROID INCLUDING ADIPOSE-DERIVED STEM CELLS AND HEPATOCYTES

CROSS-REFERENCE TO RELATED APPLICATION

This application is based on and claims priority under 35 U.S.C. § 119 to Korean Patent Application No. 10-2018-0056768, filed on May 17, 2018, in the Korean Intellectual Property Office, the disclosure of which is incorporated by reference herein in its entirety.

REFERENCE TO SEQUENCE LISTING SUBMITTED VIA EFS-WEB

This application includes an electronically submitted sequence listing in .txt format. The .txt file contains a sequence listing entitled "1183-0134PUS1_ST25.txt" created on Aug. 23, 2019 and is 1,974 bytes in size. The sequence listing contained in this .txt file is part of the specification and is hereby incorporated by reference herein in its entirety.

BACKGROUND

1. Field

The present disclosure relates to a method of preparing a three-dimensional cell spheroid, the method including forming the cell spheroid by co-culturing adipose-derived stem cells or mesenchymal stem cells with hepatocytes.

2. Description of the Related Art

Stem cells are cells having the ability to self-replicate to make copies of themselves and the ability to differentiate into specialized cells, and stem cells are able to regenerate a tissue or an organ and to differentiate according to characteristics of organs after organ transplantation. For these reasons, stem cells are suitable for regenerative medicine. Mesenchymal stem cells are a type of adult stem cell having adhesive properties, and are multipotent stem cells that can differentiate into musculoskeletal cells such as bone, cartilage, and fat cells. Mesenchymal stem cells are easily cultured in vitro, have excellent proliferative ability, and are able to differentiate into desired tissues to be used for the treatment of degenerative arthritis, spinal cord injury, myocardial infarction, diabetic diseases, etc. To use stem cells as a cellular therapeutic agent, a culture method capable of obtaining a sufficient amount of cells is required. Due to their adherent growth characteristics, mesenchymal stem cells are subjected to two-dimensional adherent culture in a flat-bottomed flask. This culture method may reduce differentiation and replication abilities which are intrinsic properties of stem cells, and may cause cell loss and contamination during adherent subculture. Further, since $1.0 \times 10^8$ cells or more are required to use stem cells in cell therapy, it is not economical to obtain a large number of cells using the two-dimensional culture method with a limited culture area. Therefore, to solve the problems of reduced space efficiency and reduced stem cell characteristics due to the two-dimensional culture method, three-dimensional suspension culture methods have been developed. Among the many three-dimensional culture methods developed to date, a method of forming embryonic bodies by inducing aggregation of embryonic stem cells is applied to culture of mesenchymal stem cells, and a three-dimensional culture method of forming spheres have been developed. When the three-dimensional culture is performed while inducing cell aggregation, intercellular signal transduction actively occurs, and the three-dimensional culture mimics in vivo environments more similarly than the two-dimensional culture method, thereby increasing the therapeutic potential of the cells.

Together with the three-dimensional culture method, a co-culture method has been also applied to a cell therapy using stem cells to enhance cell proliferation and characteristics. The co-culture method may be used to culture two or more different kinds of cells under the same environment, thereby enhancing cell proliferation or characteristics through intercellular interactions, as compared with monoculture. Accordingly, there have been various attempts to maximally enhance cell characteristics by co-culture suitable for therapeutic purposes.

SUMMARY

An aspect provides a method of preparing a three-dimensional cell spheroid, the method including adherent-culturing adipose-derived stem cells or mesenchymal stem cells in a culture plate having a hydrophobic surface; co-culturing the cells with hepatocytes by additionally seeding the hepatocytes into the culture plate; and forming the three-dimensional cell spheroid by detaching the adipose-derived stem cells or mesenchymal stem cells; and the hepatocytes from the culture plate as a density of the adherent adipose-derived stem cells or mesenchymal stem cells; and the hepatocytes increases.

Another aspect provides a cell spheroid prepared by the above method.

Still another aspect provides a cell spheroid including adipose-derived stem cells or mesenchymal stem cells; and hepatocytes.

Still another aspect provides a cellular therapeutic agent for treating a liver disease, the cellular therapeutic agent including the cell spheroid.

Still another aspect provides a pharmaceutical composition for preventing or treating a liver disease, the pharmaceutical composition including the cell spheroid and/or a culture medium thereof.

Still another aspect provides a health functional food composition for improving hepatic functions, the health functional food composition including the cell spheroid and/or the culture medium thereof.

Still another aspect provides a method of preventing or treating a liver disease, the method including administering to a subject the cell spheroid including the adipose-derived stem cells or the mesenchymal stem cells; and the hepatocytes and/or the culture medium thereof.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
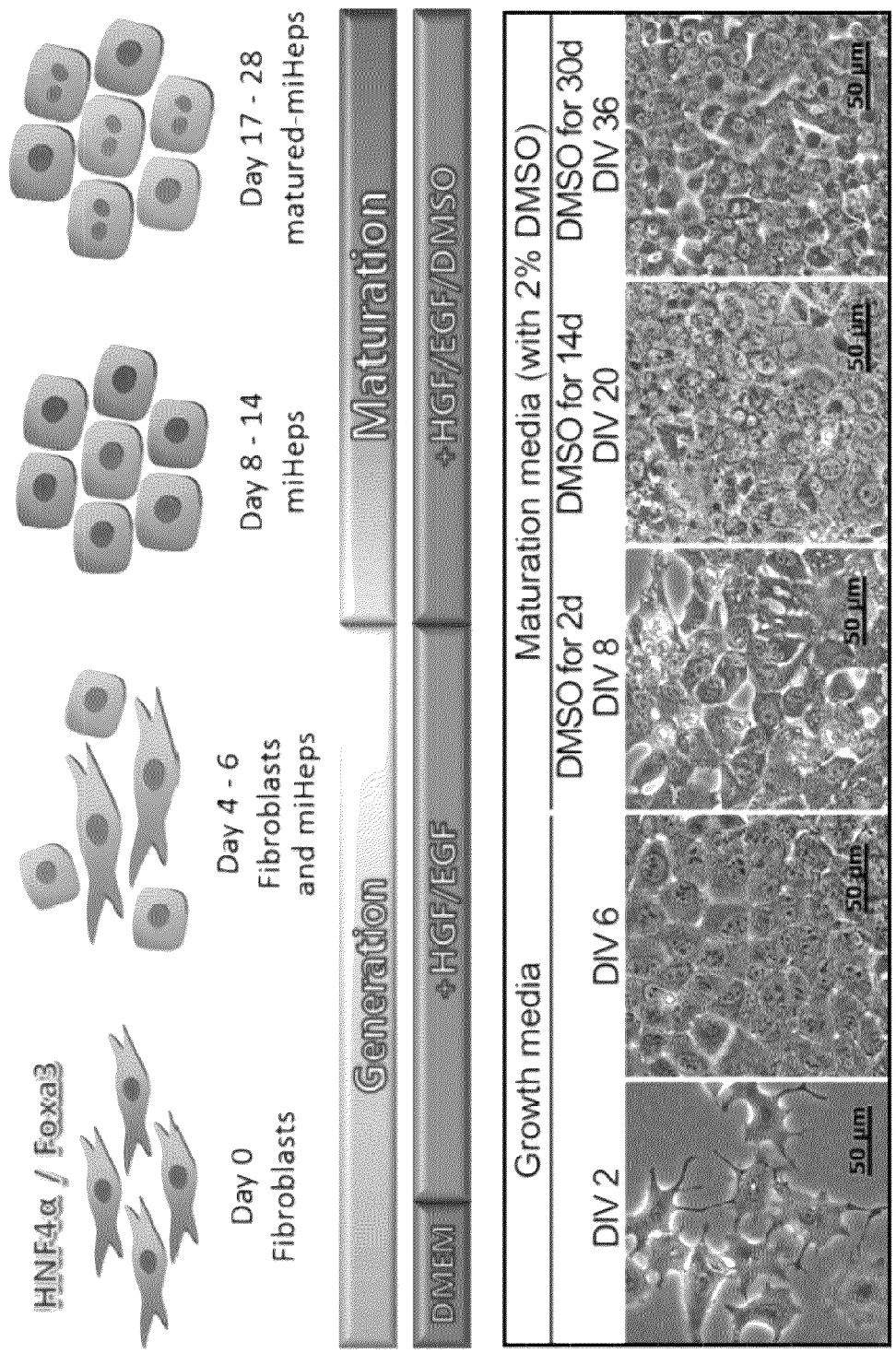
FIG. 1A illustrates a process of culturing mouse induced hepatic progenitors (miHeps) into which upstream factors were introduced.

An aspect provides a method of preparing a three-dimensional cell spheroid, the method including adherent-culturing adipose-derived stem cells or mesenchymal stem cells in a culture plate having a hydrophobic surface; co-culturing the cells with hepatocytes by additionally seeding the hepatocytes into the culture plate; and forming the three-dimensional cell spheroid by detaching the adipose-derived stem cells or mesenchymal stem cells; and the hepatocytes from the culture plate as a density of the adherent adipose-derived stem cells or mesenchymal stem cells; and the hepatocytes increases.

As used herein, the term "cell spheroid" or "three-dimensional cell spheroid" refers to a state in which two or more cells are aggregated, and may be in a tissue form or in a multicellular form. Each cell spheroid may be present as a tissue itself or as a part thereof, or may be present as a multicellular cluster. The cell spheroid may include a stromal cell-differentiated cell-like tissue.

As used herein, the term "three-dimensional" refers to a structure having a model with three geometric parameters (e.g., depth, width, and height, or X-, Y-, and Z-axes) rather than two dimensional parameters. Therefore, the cell spheroid according to a specific embodiment refer to a cell spheroid that may be cultured in a three-dimensional manner, i.e., may be cultured in a floating state while being detached from the culture plate, and three-dimensionally formed into spheres, sheets, or similar three-dimensional forms (e.g., a similar tissue) while proliferating. In addition, the three-dimensional cell spheroid may refer to a cell spheroid that is formed in a multilayer or spherical form, rather than a cell spheroid that is formed in a single cell layer like a general cell spheroid. Further, the cell spheroid according to a specific embodiment may refer to a cell spheroid formed by itself without the need to use an artificial three-dimensional porous extracellular matrix, for example, a synthetic polymer support such as a sheet, a hydrogel, a film, and a scaffold, or a natural polymeric support, by using tissue engineering techniques. The tissue engineering technique is distinguished from formation of the three-dimensional cell spheroid according to a specific embodiment in which the matrix, rather than the cell, is three-dimensional. The cell spheroid may have a diameter of 300 μm or more, for example, 300 μm to 2,000 μm, 400 μm to 1,500 μm, 500 μm to 1,000 μm, 500 μm to 900 μm, or 700 μm to 800 μm.

The adipose-derived stem cell may be isolated from a human adipose tissue. The human adipose tissue may appropriately include mature adipocytes and a connective tissue surrounding them. The human adipose tissue may be any adipose tissue obtained by any method used to collect fat regardless of the site of an individual's body. For example, the human adipose tissue may include a subcutaneous adipose tissue, a bone marrow adipose tissue, a mesenteric adipose tissue, a gastric adipose tissue, or a retroperitoneal adipose tissue. Further, isolation of the adipose-derived stem cells from the human adipose tissue may be performed by a known method. For example, the adipose-derived stem cells may be obtained from adipose tissues by liposuction, sedimentation, enzymatic treatment of collagenase, etc., removal of suspension cells such as red blood cells, etc. by centrifugation. The isolated adipose-derived stem cells or mesenchymal stem cells exhibit an excellent proliferation rate up to the passage number of 16 even after several subculturing. Therefore, in the subsequent formation of the three-dimensional cell spheroid, multipotent adipose-derived stem cells isolated from the human adipose tissue or mesenchymal stem cells may be used as they are at passage 1 or those subcultured to 60% confluency at passage 10 or more may be used.

The culture plate may be a culture plate from which the cells may be detached as the density of the cells increases due to cell-cell adhesion lower than cell-plate surface adhesion. The culture plate may be prepared by using a material containing a substance capable of non-integrin cell adhesion or may be coated with the material. The culture plate may be a culture plate that is surface-treated with a polymer imparting hydrophobicity to a common cell culture plate, or a cell culture plate prepared by such a polymer. Such a hydrophobic polymer may include, for example, one or more selected from polystyrene (PS), polymethyl methacrylate (PMMA), polyethylene terephthalate (PET), polyvinyl chloride (PVC), polyethylene (PE), polypropylene (PP), polytetrafluoroethylene (PTFE), aliphatic polyester-based polymer such as poly(L-lactic acid) (PLLA), poly(D,L-lactic acid) (PDLLA), poly(glycolic acid) (PGA), poly(caprolactone) (PCL), poly(hydroxyalkanoate), polypolydioxanone (PDS), polytrimethylene carbonate, or a copolymer of these units such as poly(lactic acid-co-glycolic acid) (PLGA), poly(lactic acid-co-caprolactone) (PLCL), poly(glycolic acid-co-caprolactone) (PGCL), or a derivative thereof. In addition, the culture plate may have a hydrophobic silanized surface, a carbon nanotube (CNT) surface, a hydrocarbon-coated surface, or a metallic (e.g., stainless steel, titanium, gold, platinum, etc.) surface.

In another specific embodiment, for more effective adhesion of the cells onto the culture plate than physical adsorption by interactions between the adipose-derived stem cells or the mesenchymal stem cells and the hydrophobic surface of the culture plate, a growth factor having adhesive activity to stromal cells is immobilized on the surface of the culture plate, and then biochemical interactions between the immobilized growth factor and cells may be used. In this regard, the growth factor may include those having adhesive activity to cells, and binding of the growth factor to the cells may be non-integrin adhesion. The growth factor may include, for example, vascular endothelial growth factor (VEGF), fibroblast growth factor (FGF), epidermal growth factor (EGF), platelet-derived endothelial growth factor (PDGF), hepatocyte growth factor (HGF), insulin-like growth factor (IGF), heparin binding domain (HBD), and fragments thereof having cell adhesive activity. Further, the growth factor may be immobilized on the surface of the culture plate at a concentration of 5 μg/ml to 30 μg/ml, for example, 5 μg/ml to 30 μg/ml, 5 μg/ml to 25 μg/ml, 10 μg/ml to 30 μg/ml, 10 μg/ml to 25 μg/ml, or 10 μg/ml to 20 μg/ml. Further, in another specific embodiment, the co-culture may be performed for 20 hours to 60 hours, for example, 20 hours to 60 hours, 20 hours to 50 hours, 20 hours to 50 hours, 30 hours to 45 hours, 30 hours to 40 hours, or 24 hours to 48 hours. In this regard, when the culture time is less than the above range, there is a problem in that the cultured cells do not completely aggregate as a spheroid. When the culture time exceeds the above range, there is a problem in that viability of the cell spheroid decreases.

Further, the surface of the culture plate may be additionally coated with an artificial ligand. The artificial ligand may be an artificial ligand specific to hepatocytes, and has an amphipathic property. For example, when the surface of the culture plate may be coated with PVLA as the artificial ligand, frequency of hepatocyte spheroid formation may be increased because the PVLA has a site capable of binding to the surface of the hepatocyte and a site capable of binding to the polystyrene surface. In this regard, the artificial ligand may be, for example, a polystyrene derivative including a residue such as PVMeA, PVCA, PV6Gna, galactose/N-acetyl D-galactosamine, etc. and having a hepatocyte-specific receptor binding ability.

Another aspect provides a three-dimensional cell spheroid prepared by the above method. The cell spheroid may have a multilayer or a spherical form which is formed by the adipose-derived stem cells or mesenchymal stem cells and the hepatocytes, and may include $1\times10^4$ cells to $1\times10^5$ cells, for example, $1\times10^4$ cells to $1\times10^5$ cells, $1\times10^4$ cells to $9\times10^4$ cells, $1\times10^4$ cells to $8\times10^4$ cells, $1\times10^4$ cells to $5\times10^4$ cells, $3\times10^4$ cells to $1\times10^5$ cells, or $4\times10^4$ cells to $1\times10^5$ cells per 700 μm to 800 μm of the diameter of the cell spheroid.

Still another aspect provides a three-dimensional cell spheroid including adipose-derived stem cells or mesenchymal stem cells; and hepatocytes. A specific description of the cell spheroid is the same as above.

Further, the adipose-derived stem cells or the mesenchymal stem cells; and the hepatocytes may be mixed at a ratio of 1:5 to 5:1. For example, the adipose-derived stem cells or the mesenchymal stem cells; and the hepatocytes may be mixed at a ratio of 1:5 to 5:1, 1:4.5 to 4.5:1, 1:3.5 to 3.5:1, 1:3 to 3:1, 1:2 to 2:1, or 1:1 to 2:1. In this regard, when the mixing ratio of the cells is less than the above range, there is a problem in that the culture cells may not form one spheroid but may be fragmented. When the mixing ratio of the cells exceeds the above range, there is a problem in that hepatic characteristics of the cell spheroid may be reduced due to the reduced amount of hepatocytes included in the cell spheroid.

Still another aspect provides a cellular therapeutic agent for treating a liver disease, the cellular therapeutic agent including the cell spheroid. A specific description of the cell spheroid is the same as above. Still another aspect provides a method of preventing or treating a liver disease, the method including administering the cellular therapeutic agent to a subject. In a specific embodiment, the method may further include a culture medium of the cell spheroids including the adipose-derived stem cells or the mesenchymal stem cells; and the hepatocytes.

As used herein, the term "cellular therapeutic agent" refers to a drug (US FTA regulation) which is cells or tissues isolated from humans, cultured and produced through special manipulations and is used for the purpose of treatment, diagnosis, and prevention, and refers to a drug obtained by proliferating and selecting living autologous, allogeneic, or xenogeneic cells ex vivo or by a series of actions, such as alteration of biological properties of the cells in different ways, in order to restore functions of cells or tissues, and used for the purpose of treatment, diagnosis, and prevention of a disease.

Specifically, the cellular therapeutic agent of a specific embodiment may be used for treating liver diseases including hepatitis, hepatotoxicity, cholestasis, fatty liver, cirrhosis, liver ischemia, alcoholic liver disease, etc.

Still another aspect provides a pharmaceutical composition for preventing or treating the liver disease, the pharmaceutical composition including the cell spheroid and/or the culture medium thereof. A specific description of the cell spheroid is the same as above.

The culture medium refers to a solution that is remained by removing cell spheroids after culturing the adipose-derived stem cells or the mesenchymal stem cells; and the hepatocytes for a predetermined period in a medium capable of supporting growth and survival of separated cell spheroids in vitro, and the culture medium may include all of proteins such as growth factors and cytokines secreted from cells during a culture period and nutrients remaining after being consumed during culture. Specifically, the culture medium is a medium obtained from the culture medium where the adipose-derived stem cells or the mesenchymal stem cells are cultured in a three-dimensional manner, and may include a substance promoting hepatocyte division and maturation, for example, secretome, etc. Further, the liver disease may be selected from the group consisting of hepatitis, hepatotoxicity, cholestasis, fatty liver, cirrhosis, liver ischemia, alcoholic liver disease, hepatic abscess, hepatic coma, hepatatrophia, and hepatic cancer.

In a specific embodiment, when the cell spheroid formed in a diameter of 700 μm to 800 μm is defined as 1 unit, the cell spheroid may be mixed at a ratio of 1 unit per 100 µl to 500 µl, for example, 100 µl to 500 µl, 100 µl to 400 µl, 150 µl to 500 µl, 150 µl to 450 µl, or 150 µl to 350 µl of the culture medium. In this regard, when the mixing ratio is less than the above range, there is a problem in that it is difficult to obtain the prophylactic or therapeutic effect on liver diseases.

The pharmaceutical composition for preventing or treating liver diseases according to still another aspect may be used after being prepared in an oral formulation such as a powder, a granule, a tablet, a capsule, a suspension, an emulsion, a syrup, an aerosol, etc., or in a formulation for external use, a suppository, or a sterile injectable formulation according to common methods. For the preparation, the pharmaceutical composition may include an appropriate carrier, excipient, or diluent commonly used in the preparation of pharmaceutical compositions.

The carrier, excipient, or diluent may include a variety of compounds such as lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, etc., or a mixture thereof.

Upon preparation, the formulation may be prepared using a commonly used diluent or excipient such as a filler, an extender, a binder, a wetting agent, a disintegrant, a surfactant, etc.

A solid formulation for oral administration may be prepared by mixing the cell spheroid and/or the culture medium thereof with one or more excipients, such as starch, calcium carbonate, sucrose, lactose, gelatin, etc. In addition to simple excipients, lubricants such as magnesium stearate, talc, etc. may be used.

A liquid formulation for oral administration may include a suspension, a solution for internal use, an emulsion, a syrup, etc. and may include various kinds of excipients, e.g., humectants, sweeteners, fragrances, preservatives, etc., in addition to simple diluents commonly used, such as water and liquid paraffin.

A formulation for parenteral administration may include a sterile aqueous solution, a non-aqueous solvent, a suspension, an emulsion, a lyophilized preparation, and a suppository. For the non-aqueous solvent and the suspension, propylene glycol, polyethylene glycol, a vegetable oil such as olive oil, and an injectable ester such as ethyl oleate may be used. As a base for suppositories, witepsol, macrogol, Tween 61, cacao butter, laurin butter, glycerogelatin, etc. may be used.

An administration dose of the pharmaceutical composition for preventing or treating liver diseases according to still another aspect may vary depending on a patient's conditions, body weight, disease severity, a type of a drug, administration route and period, but may be appropriately selected by those skilled in the art. However, for better effects, the administration dose may be 0.0001 mg/kg to 2,000 mg/kg, 0.001 mg/kg to 2,000 mg/kg per day. The administration may be performed once or several times a day. However, the scope of the present disclosure is not limited to the above administration dose.

The pharmaceutical composition for preventing or treating liver diseases according to still another aspect may be administered to mammals such as rats, mice, livestock, humans, etc. via various routes. All modes of administration may be contemplated, for example, administration may be made orally, rectally or by intravenous, intramuscular, subcutaneous, endometrial, or intracerebroventricular injection.

Still another aspect provides a health functional food composition for improving hepatic functions, the health functional food composition including the cell spheroid and/or the culture medium thereof. Specific descriptions of the cell spheroid and the culture medium thereof are the same as above.

With regard to the health functional food for improving hepatic functions according to still another aspect, when the cell spheroid and/or the culture medium thereof is used as an additive of the health functional food, it may be used as it is or together with another food or food ingredients and may be appropriately used according to a common method. A mixing amount of the effective ingredients may be appropriately determined according to the purpose of use such as prevention, health, or treatment.

The health functional food may be in a formulation of any one of general foods or beverages as well as in a formulation of a powder, a granule, a pill, a tablet, or a capsule.

The kind of the food is not particularly limited, and examples of the food to which the above substance may be added may include meats, sausages, breads, chocolates, candies, snacks, cookies, pizzas, ramen, other noodles, gums, dairy products including ice cream, various kinds of soups, beverages, teas, drinks, alcoholic beverages, vitamin complexes, etc., and may include all kinds of foods from the common point of view.

Generally, during preparation of foods or beverages, the cell spheroid and/or the culture medium thereof may be added in an amount of 15 parts by weight or less, or 10 parts by weight or less, based on 100 parts by weight of raw materials. However, in the case of a long-term intake of the food for the purpose of health and hygiene or for health control, the amount may be less than the above range. Further, since the present disclosure has no safety problem in terms of using a fraction of a natural product, the amount may be more than the above range.

Among the health functional foods according to still another aspect, the beverage may include additional ingredients such as various flavoring agents, natural carbohydrates, etc., as in common beverages. The natural carbohydrates may include monosaccharides such as glucose, fructose, etc., disaccharides such as maltose, sucrose, etc., polysaccharides such as dextrin, cyclodextrin, etc., and sugar alcohols such as xylitol, sorbitol, erythritol, etc. As flavoring agents, natural flavoring agents such as taumatin or stevia extracts, or synthetic flavoring agents such as saccharin or aspartame may be used. A proportion of the natural carbohydrates may be about 0.01 g to about 0.04 g, or about 0.02 g to about 0.03 g per 100 mL of the beverage according to the present disclosure.

Additionally, the health functional food for improving hepatic functions according to the present disclosure may include a variety of nutrients, vitamins, electrolytes, flavoring agents, colorants, pectic acid or salts thereof, alginic acid or salts thereof, organic acids, protective colloidal thickening agents, pH modifiers, stabilizers, preservatives, glycerin, alcohols, carbonating agents used in carbonated beverages, etc. Additionally, the composition for improving hepatic functions may include fruit flesh for the preparation of natural fruit juices, fruit juice beverages, and vegetable beverages. These ingredients may be used independently or in a mixture. A proportion of these additives may be, but is not limited to, generally selected from the range of 0.01 part by weight to 0.1 part by weight with respect to 100 parts by weight of the health functional food of the present disclosure.

In a method of preparing a cell spheroid according to an aspect, adipose-derived stem cells and hepatocytes are co-cultured, and therefore, secretome secreted by the adipose-derived stem cells affects maturation of hepatocytes, thereby enhancing hepatic functions of the finally formed three-dimensional cell spheroids, i.e., organoids. Further, a composition including a culture medium of the adipose-derived stem cells may prevent or treat liver diseases including hepatitis, hepatotoxicity, cholestasis, fatty liver, etc., and may enhance hepatic functions.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

Hereinafter, preferred examples will be provided for better understanding of the present disclosure. However, the following examples are provided only for understanding the present disclosure more easily, but the content of the present disclosure is not limited thereby.

EXAMPLE

Example 1. Direct Induction of Hepatocyte Phenotype from Mouse Induced Hepatic Progenitor To obtain a large amount of mature hepatocytes which are required in the liver tissue engineering, mouse induced hepatic progenitors (miHeps) directly trans-differentiated from mouse embryonic fibroblast (MEF) were used. In detail, the cells were obtained by introducing, using a pMX viral vector, two factors of Foxa3 and HNF4a, which are known to hepatocyte-specific upstream regulating factors, into MEFs which were obtained by primary culture in E16.5 mouse.

Fibroblasts were cultured in a DMEM medium for 3 days, and then miHep were seeded at a density of $2 \times 10^4$ cells/cm$^2$ and cultured in a hepatocyte growth medium containing 20 ng/ml of HGF and 20 ng/ml of EGF for 7 days. Thereafter, the miHeps were isolated and cultured in a hepatocyte maturation medium containing 20 ng/ml of HGF, 20 ng/ml of EGF, and 2% DMSO 2% volume/volume (medium) for 7 days to 28 days.

To verify hepatocyte-specific phenotype of the hepatic progenitors, western blotting, RT-PCR, and immunostaining were performed to identify changes in cell morphology and hepatocyte-specific gene expression while increasing the cell culture time. Further, relative expression of related genes was quantified.

FIG. 1A illustrates a process of culturing miHeps into which upstream factors were introduced.

As shown in FIG. 1A, it was confirmed that as miHeps introduced with upstream factors continued to grow, the cells continued to divide and all the cells were connected on a two-dimensional culture plate to form a monolayer.

Figure 1B:
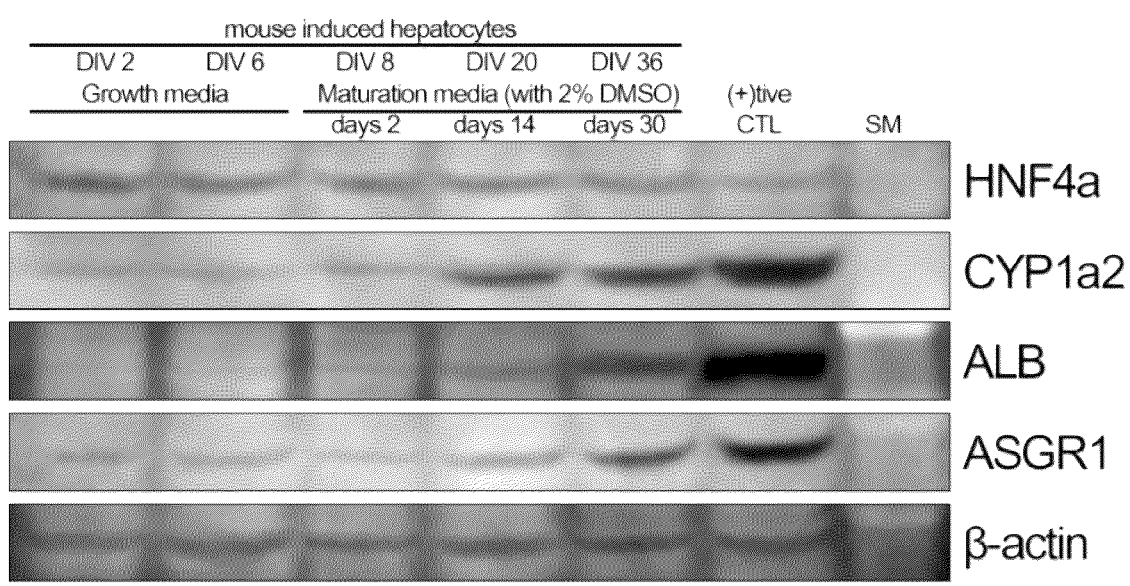
FIG. 1B shows the result of RT-PCR performed according to long-term culture of miHeps (Days in vitro; DIV 8-36)

FIG. 1B shows results of RT-PCR performed according to long-term culture of miHeps (Days in vitro; DIV 8-36).

As shown in FIG. 1B, it was confirmed that hepatocyte-specific markers were expressed, and the hepatocyte-specific gene expression was gradually increased over culture time.

Figure 1C:
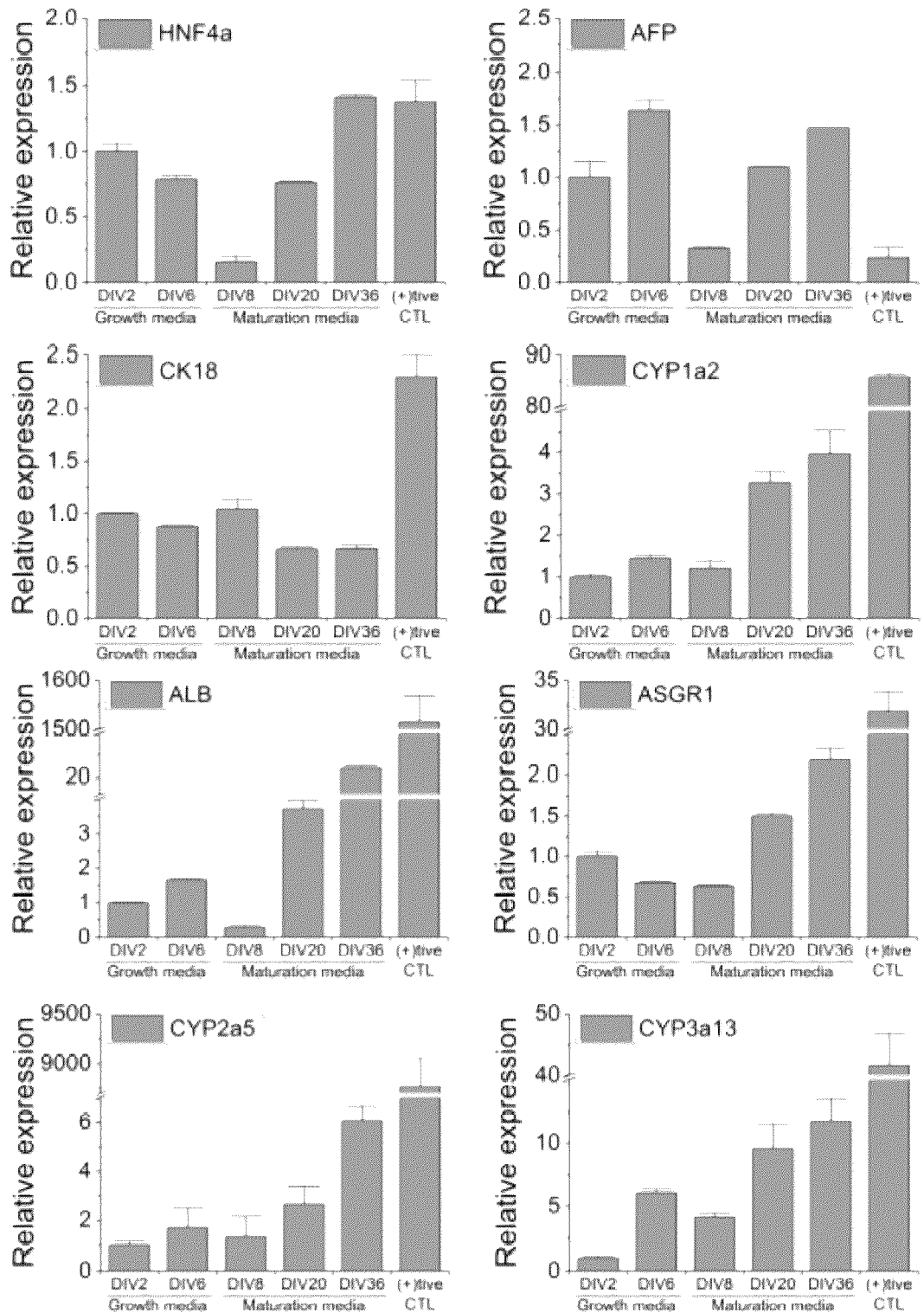
FIG. 1C is a graph showing quantification of relative expression of related genes.

FIG. 1C is a graph showing quantification of relative expression of related genes.

As shown in FIG. 1C, as the culture of miHeps was continued, particularly, after cells were connected to each other, expression of hepatocyte-specific genes such as hepatocyte nuclear factor 4 alpha (HNF4α), alpha-fetoprotein (AFP), albumin (ALB), asialoglycoprotein Receptor 1 (ASGR1), and Cytochromes P450 (CYP450) were significantly increased under specific culture conditions for inducing maturation.

These results indicate that miHeps directly trans-differentiated are able to divide and mature under specific medium conditions, and induced to mature hepatocyte-like cells by long-term culture.

Example 2. Formation of hASC-miHep Organoid 2-1. Isolation of Human Adipose-Derived Mesenchymal Stem Cell Multipotent stem cells were isolated from a human subcutaneous adipose tissue. A subcutaneous adipose tissue of a normal person was washed with PBS containing 2% penicillin/streptomycin three times to remove contaminated blood, and chopped with operating scissors. The adipose tissue was immersed in a tissue lysis buffer previously prepared (serum-free DMEM+1% BSA(w/v)+0.3% collagenase type I) and stirred at 37° C. for 2 hours, and then centrifuged at 1,000 rpm for 5 minutes to separate a supernatant and a pellet. Thereafter, the supernatant was discarded, and the pellet was collected and washed with PBS, and then centrifuged at 1,000 rpm for 5 minutes to separate a supernatant. The separated supernatant was filtered through a 100 μm mesh to remove cell debris, and the resultant was washed with PBS. The separated cells were cultured in a 10% FBS-containing DMEM/F12 medium (Welgene) for 24 hours. Then, non-adherent cells were removed by PBS washing, and cultured while replacing the 10% FBS-containing DMEM/F12 medium every two days, thereby obtaining human subcutaneous adipose tissue-derived stem cells (hASC, human adipose-derived mesenchymal stem cells).

2-2. Preparation of Three-Dimensional Cell Spheroid

To form liver-organoids by three-dimensional cell culture, three-dimensional cell spheroids (hASC-miHep organoids) were prepared from miHeps obtained in Example 1 and hASCs obtained in Example 2-1. A polypeptide linker was fused to the amino terminus of fibroblast growth factor (FGF2) having adhesive activity to stem cells to prepare a recombinant protein having adhesive activity to stem cells. miHeps obtained in Example 1 and hASCs were co-cultured using the amino terminus of the polypeptide linker of the recombinant protein on a non-tissue culture matrix (polystyrene-maltose-binding protein-basic fibroblast growth factor 2(PS-MBP-FGF2) matrix) having a hydrophobic surface, thereby forming organoids. In detail, hASCs obtained in Example 1-2 were seeded at a density of $0.5 \times 10^5$ cells/cm$^2$ on the matrix, and then incubated for 2 hours. Thereafter, miHeps obtained in Example 1 were seeded at a density of $0.5 \times 10^5$ cells/cm$^2$, and then further incubated for 2 days.

Figure 2:
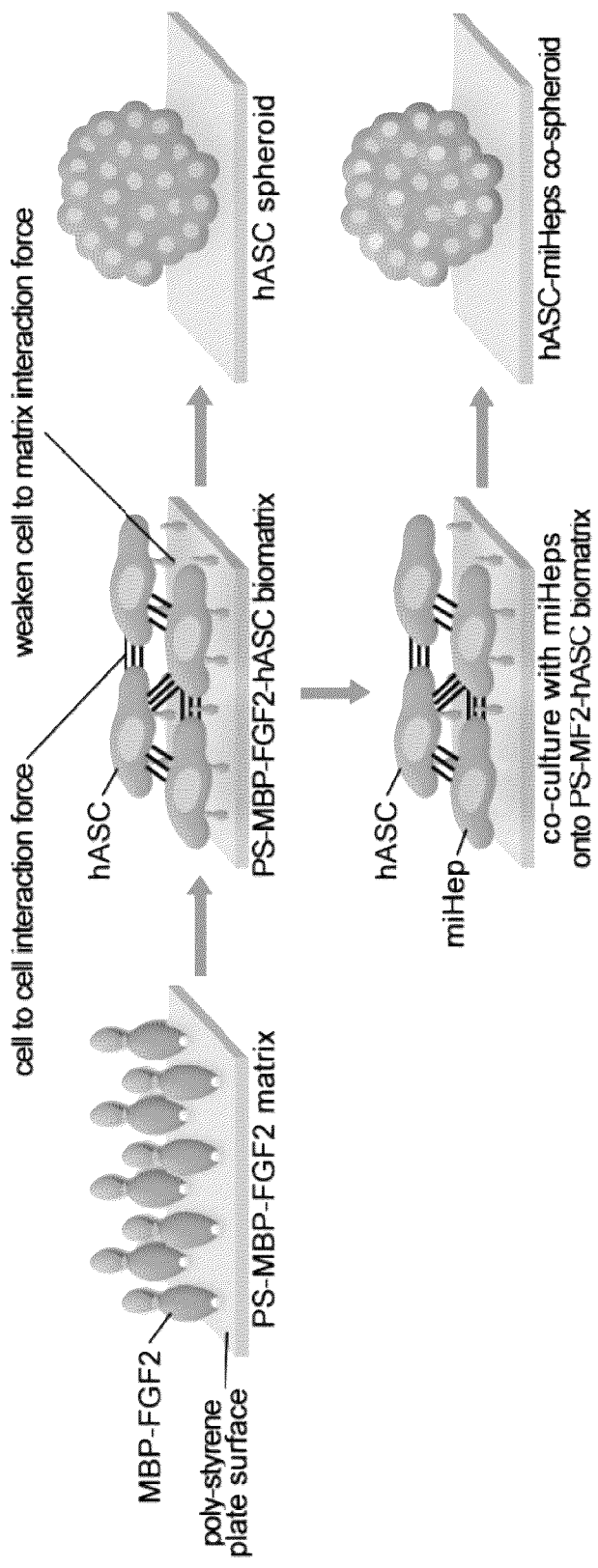
FIG. 2 illustrates a method of preparing three-dimensional cell spheroids.

FIG. 2 illustrates the method of preparing three-dimensional cell spheroids of a specific embodiment.

As shown in FIG. 2, it was confirmed that hASCs obtained in Example 1-2 formed cell-to-cell interaction and grew while adhering to MBP-FGF2 on the matrix, and a three-dimensional cell spheroid was formed with increasing density of hASCs themselves. Further, additionally seeded miHeps formed cell-to-cell interaction with hASCs, and grew while adhering to MBP-FGF2 on the matrix. Thereafter, with increasing density of hASCs and miHeps, they were detached from the surface of the matrix to form a three-dimensional cell spheroid. In this regard, the hASCs serve to provide contractile activity such that miHeps on the matrix are allowed to normally form the organoid.

Comparative Example miHeps cultured in Example 1 and hASCs obtained in Example 2-1 were two-dimensionally cultured to prepare a cell spheroid. In detail, adipose-derived stem cells obtained in Example 2-1 were seeded at a density of $0.5 \times 10^5$ cells/cm² per well in a 48-well tissue culture plate (TCP), and then incubated in a 10% FBS-containing DMEM/F12 medium for 2 hours. Thereafter, the hepatocytes cultured in Example 1 were additionally seeded at a density of $0.5 \times 10^5$ cells/cm² and cultured for 2 days.

Figure 3A:
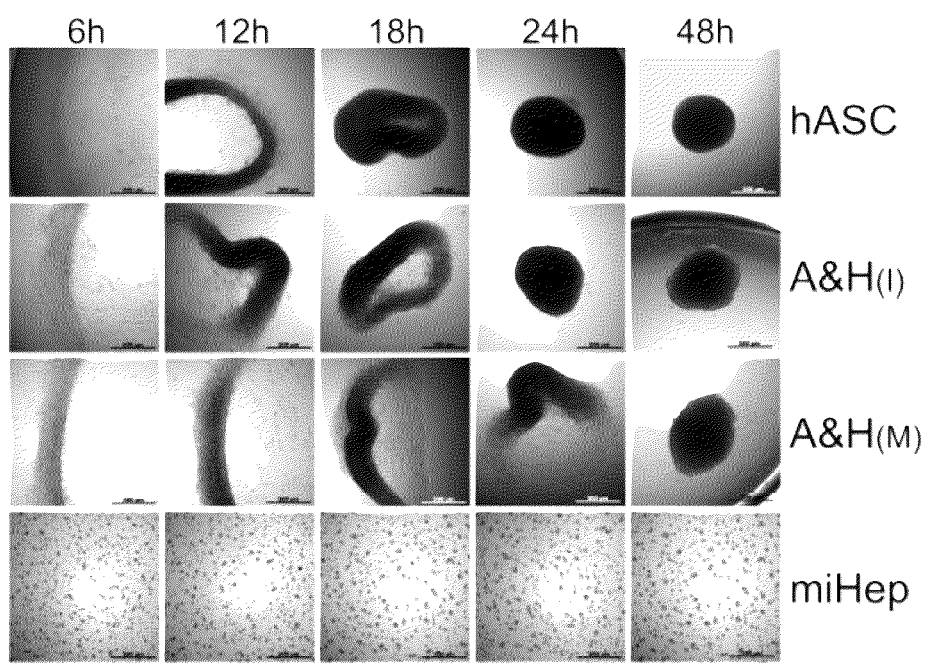
FIGS. 3A and 3B are images showing formation of three-dimensional cell spheroids.
Figure 3B:
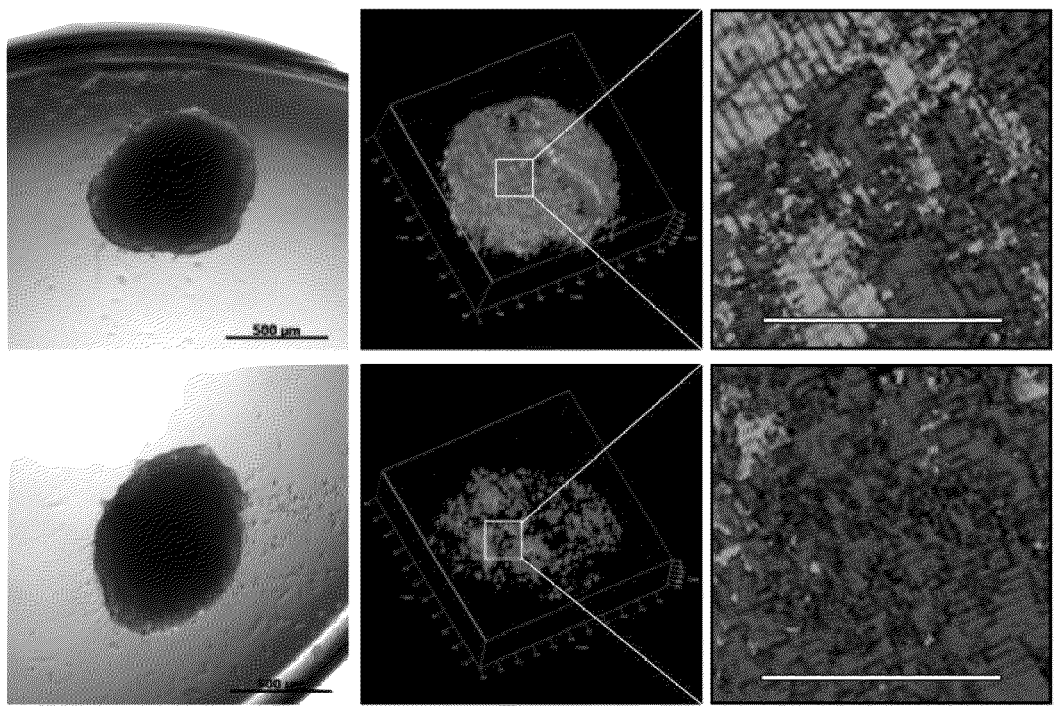

FIGS. 3A and 3B are microscopic images showing formation of three-dimensional cell spheroids according to a specific embodiment.

As shown in FIGS. 3A and 3B, it was confirmed that three-dimensional cell spheroids having a size of 700 μm to 800 μm or more as detectable with the naked eye were formed. As shown in FIG. 3B, it was confirmed that the cell spheroids have homogenous cell distribution of hASCs and miHeps without any special heterogeneity between co-cultured xenogeneic cells.

Example 2. Identification of Hepatocyte-Specific Marker Expression of Three-Dimensional Cell Spheroid Expression of hepatocyte-specific markers of the three-dimensional cell spheroid (hASC-miHep organoid) prepared in Example 1-3, miHeps of Example 1-1, and the two-dimensional cell spheroid (hASC-miHep organoid) prepared in Comparative Example 1 was analyzed by RT-PCR and real-time PCR. Media for miHeps are divided into a growth medium that preferentially promotes cell division so as to enable large-scale culture during a culturing process and a maturation medium that induces cell maturation while suppressing division. Therefore, miHeps were cultured under the respective conditions and divided into two different miHeps which are different in maturity. In detail, from the cell spheroid prepared using immature miHeps cultured in the hepatocyte maturation medium of Example 1 and the cell spheroid prepared using mature miHeps obtained in Example 1, total RNAs were extracted and purified at 2 days after culture using a TRIzol reagent (Invitrogen, Carlsbad, CA, USA), chloroform (Sigma, St. Louis, MO, USA), and 100% isopropanol (Sigma, St. Louis, MO, USA) in accordance with the manufacturer's protocol. The extracted RNAs were dissolved in nuclease-free water, and cDNAs were synthesized using Maxime RT PreMix (iNtRon, Korea) in accordance with the manufacturer's protocol. 0.2 mM of dNTP mix (Promega), 10 pmol of target gene (vWF, CD34, PECAM1, and VEGF)-specific primers, and 0.25 unit of Taq DNA polymerase (Promega, M791A) were amplified in ABI Prism 7500 (Applied Biosystems), and the resulting PCR products were electrophoresed on a 2% agarose gel at 100 V for 40 minutes. The conditions and information of the used primers are shown in Table 1 below.

TABLE 1

| Gene | Primer | SEQ ID NO. | Nucleotide sequence (5'→3') | Size (bp) | Annealing temperature (° C.) |
| --- | --- | --- | --- | --- | --- |
| HNF4α | F | 1 | ATCGTCAAGCCTCCCTCTGC | 26 | 55 |
|  | R | 2 | GACTGGTCCCTCGTGTCACATC | 22 |  |
| CYP1a2 | F | 3 | AGGAGCTGGACACGGTGGTT | 20 | 55 |
|  | R | 4 | AGGTGTCCCTCGTTGTGCTG | 20 |  |
| ALB | F | 5 | GGCTACAGCGGAGCAACTGA | 20 | 55 |
|  | R | 6 | GCCTGAGAAGGTTGTGGTTGTG | 22 |  |
| ASGR1 | F | 7 | GGTGACCTCCAGGGATGAGCAGAAC | 25 | 60 |
|  | R | 8 | CTGTTCCATCCACCCATTTCCAGGGC | 26 |  |

Figure 4A:
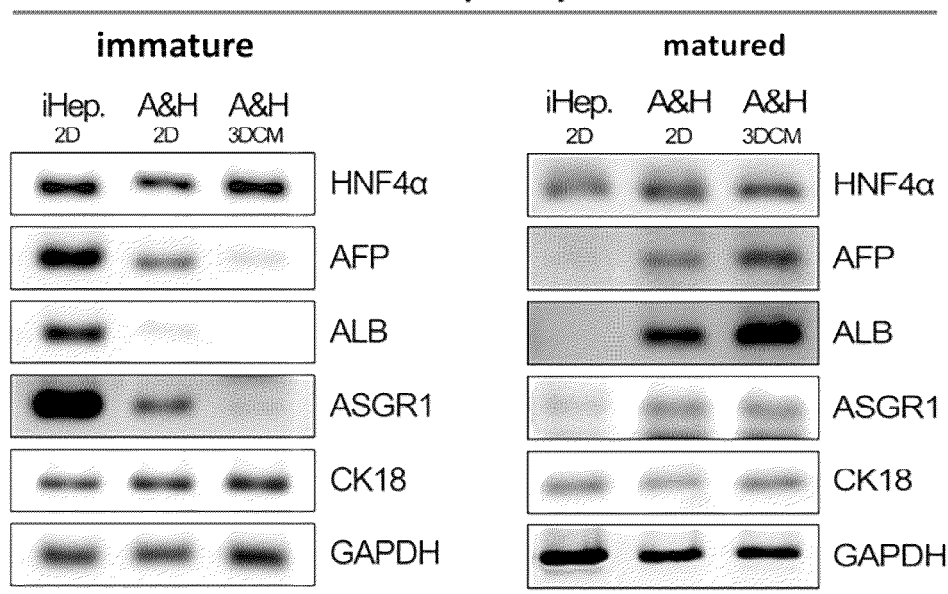
FIGS. 4A and 4B show the results of analyzing hepatocyte-specific marker expression in cell spheroids.

As shown in FIG. 4A, the immature hASC-miHeps organoid cultured in the growth medium showed a gradual reduction in the expression of hepatocyte-specific genes such as AFP, ALB and ASGR1 as two- and three-dimensional cultures were proceeded under co-culture conditions, as compared with miHeps cultured alone. However, mature hASC-miHeps organoid prepared using miHeps of which maturation was induced using the maturation medium showed increased expression of the genes as two- and three-dimensional cultures were proceeded under co-culture conditions. In other words, in the co-cultured cell spheroids, hASCs may ambivalently modulate the hepatocyte-specific functions of miHeps according to the maturity of miHeps.

Figure 4B:
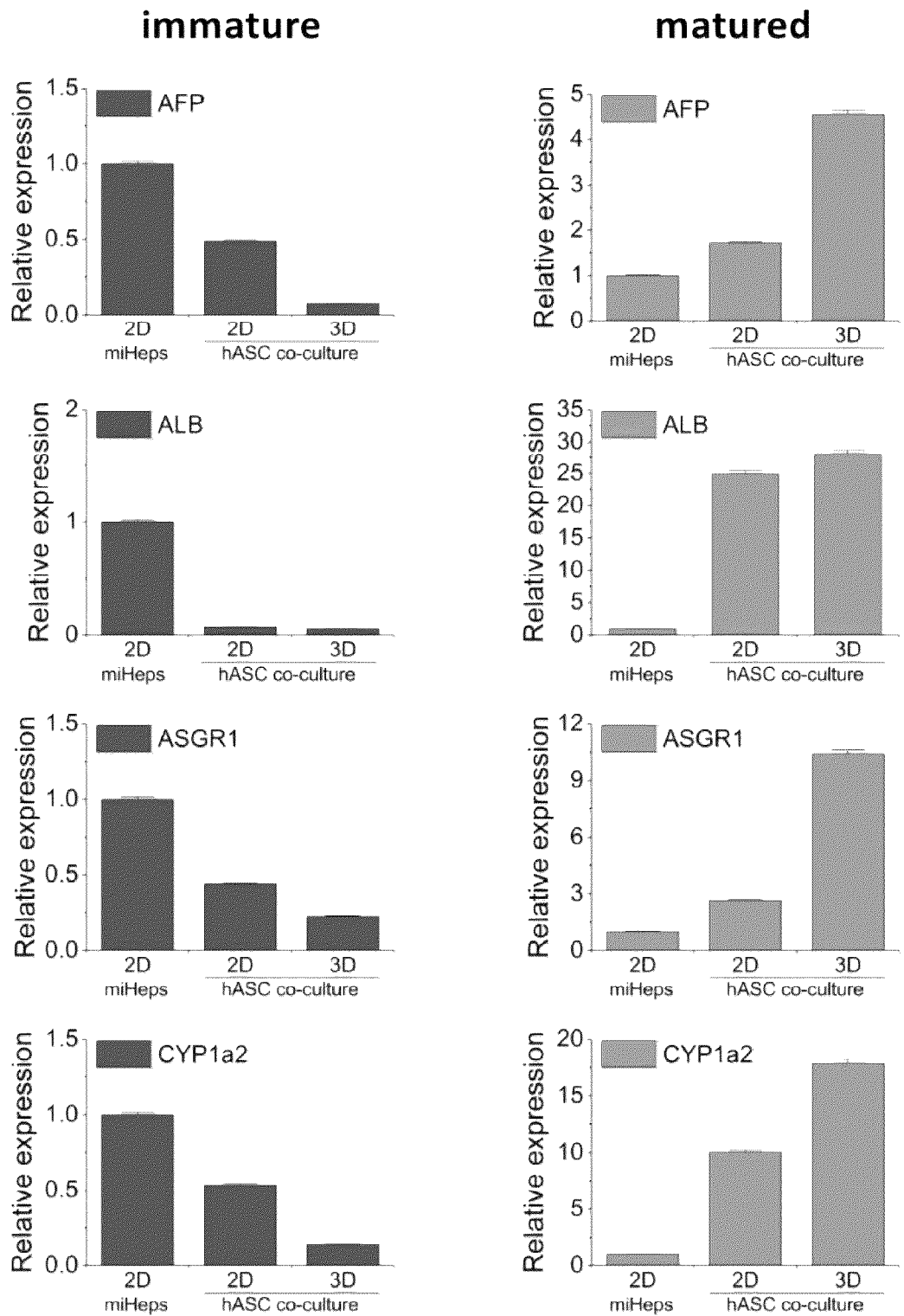

Additionally, relative expression of related genes was quantified. As shown in FIG. 4B, with regard to the immature cell spheroids, the three-dimensionally cultured cell spheroid showed low levels of marker expression, as compared with the two-dimensionally cultured cell spheroid. Further, when cultured in the same manner, mature hASC-miHeps organoid showed increased expression of AFP, ALB, ASGR1, and CYP1α2, as compared with immature hASC-miHeps organoid. With regard to the mature hASC-miHeps organoid, the three-dimensionally cultured cell spheroid showed high levels of marker expression, as compared with the two-dimensionally cultured cell spheroid.

Example 3. Characterization of Culture Medium of Three-Dimensional Cell Spheroid To examine whether ambivalent modulation of hepatocyte-specific gene expression according to the maturity of miHeps in the co-cultured hASC-miHep organoid is attributed to factors secreted by hASCs, immature or mature miHeps cultured under two dimensional conditions were treated with conditioned medium (CM) obtained from hASCs which were cultured under two- or three-dimensional conditions. Media used in the two- or three-dimensional culture to obtain the conditioned medium were all CB-ADMSC-GM of CEFO Co. Ltd., and the adipose-derived stem cells obtained in Example 2-1 were seeded at a density of $1.0 \times 10^5$ cells/cm² in a 98-well tissue culture plate (TCP) or a 98-well non-tissue culture plate (NTCP) coated with MBP-FGF2, and additionally cultured for one day, thereby obtaining the tissue culture media. Thereafter, hepatocyte-specific gene expression of miHeps was examined by RT-PCR and real-time PCR. Further, to visualize the effects of the conditioned culture media on division of mature or immature miHeps and albumin, Ki-67 and albumin expression in miHeps treated with the hASC conditioned culture media was examined by immunostaining.

Figure 5A:
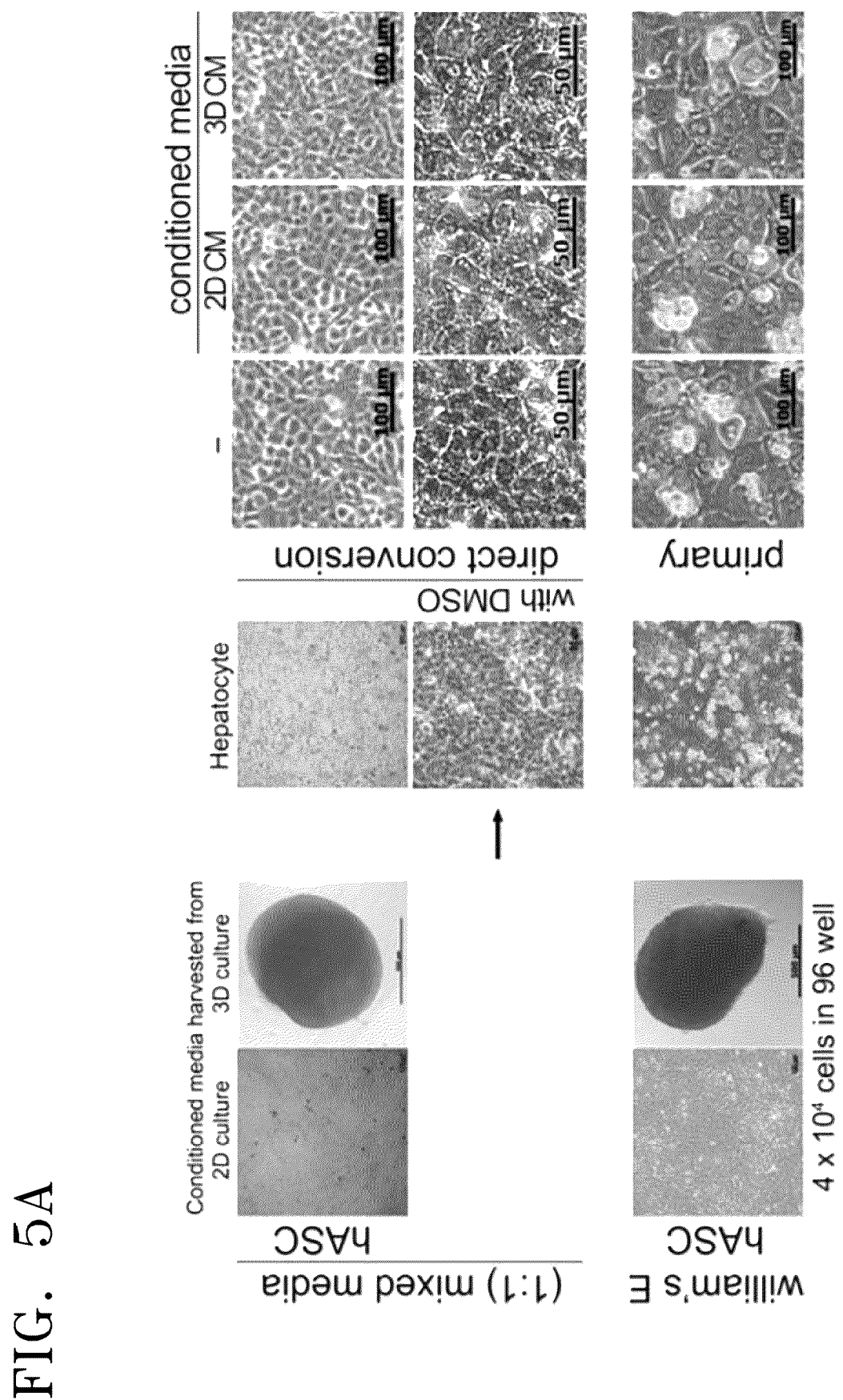
FIG. 5A shows images showing the result of treating two-dimensionally cultured miHeps with conditioned culture media.
Figure 5B:
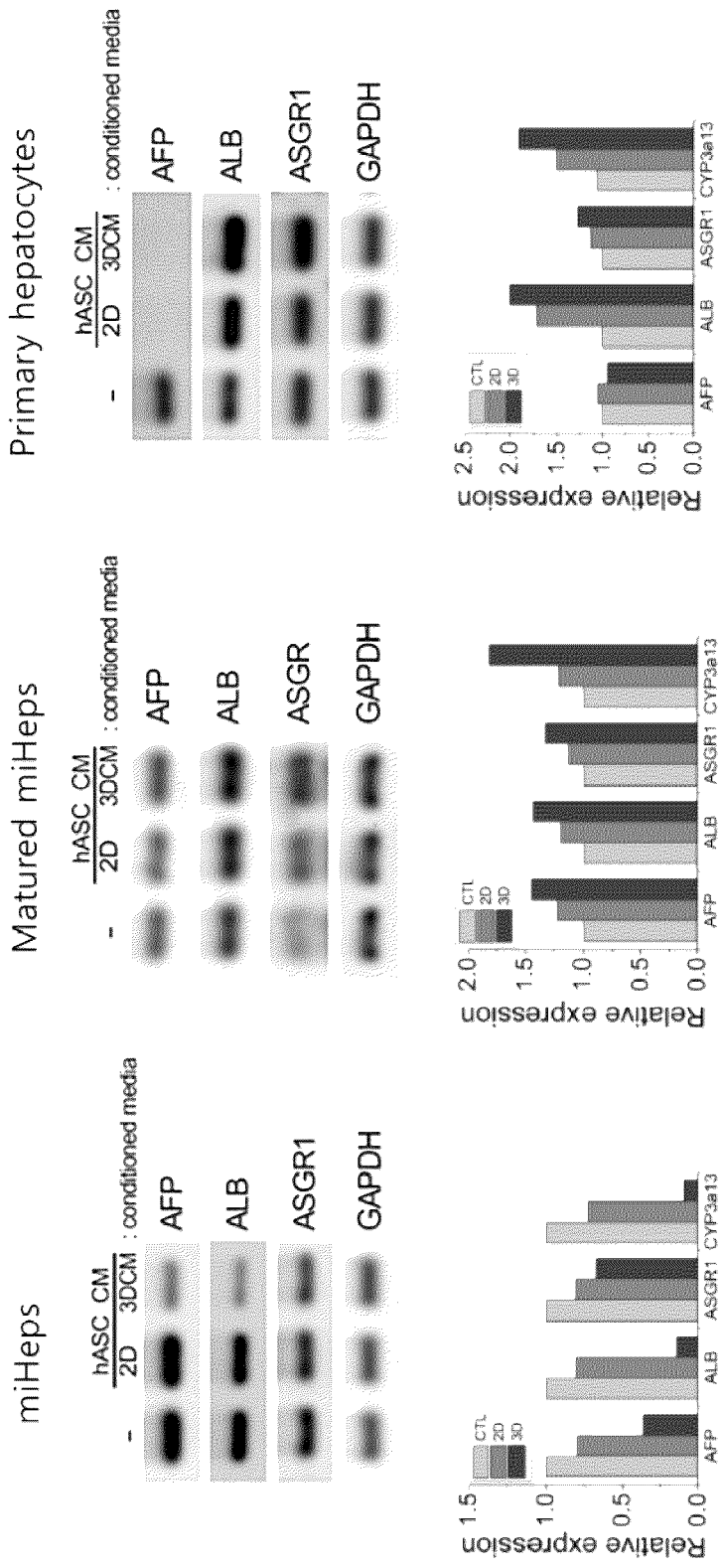
FIG. 5B shows the result of examining hepatocyte-specific gene expression of miHeps.

FIG. 5A shows images showing the result of treating the two-dimensionally cultured miHeps with the conditioned culture media, and FIG. 5B shows the result of examining hepatocyte-specific gene expression of the miHeps.

As shown in FIG. 5A, there was no particular changes in the morphology of the mature or immature miHeps treated with the conditioned culture media. However, as shown in FIG. 5B, the ambivalent modulation according to the maturity of miHeps, which was observed when miHeps and hASCs were co-cultured in Example 2, was also reproduced. This modulation phenomenon was strongly observed in miHeps which were treated with the conditioned medium of hASCs cultured three-dimensionally.

Figure 5C:
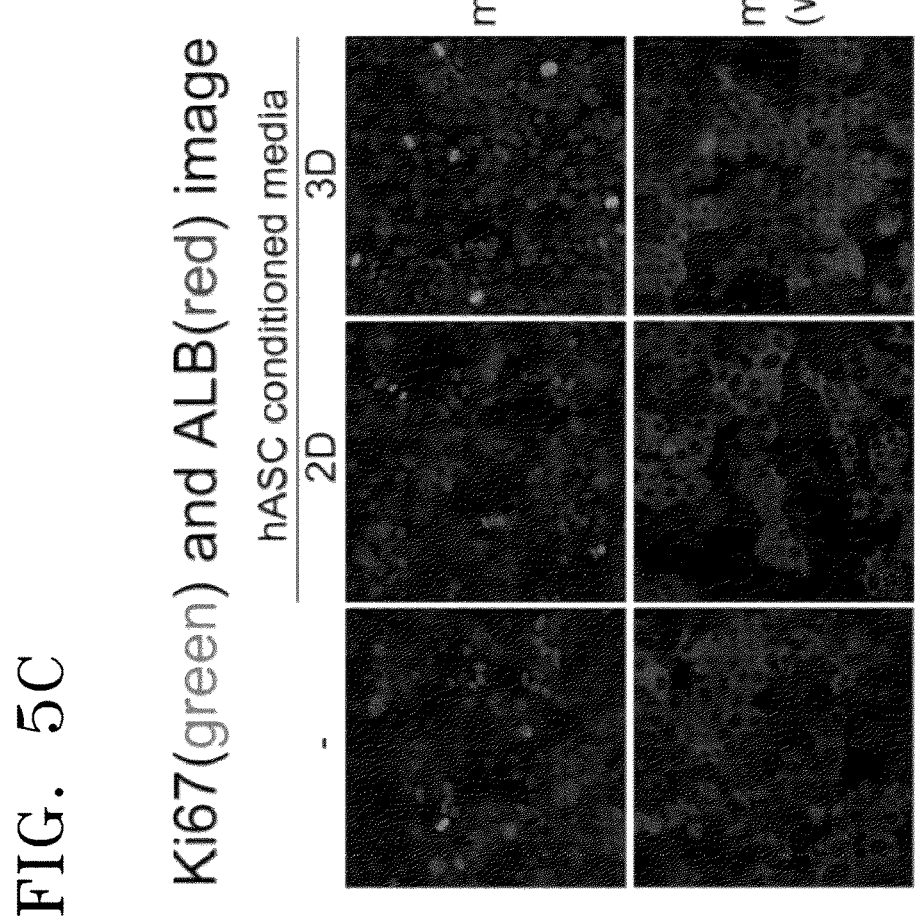
FIG. 5C shows the result of examining Ki-67 and albumin expression patterns of miHeps treated with the conditioned media.

FIG. 5C shows the result of examining Ki-67 and albumin expression patterns of miHeps treated with the conditioned medium. As shown in FIG. 5c, when the immature miHeps were treated with the conditioned medium of hASCs cultured two-dimensionally, it was difficult to identify a great expression difference in both the Ki-67⁺ cells and albumin⁺ cells. However, when treated with the conditioned medium of hASCs cultured three-dimensionally, the number of the Ki-67⁺ cells was greatly increased, and the number of albumin⁺ cells was relatively rather decreased. On the contrary, since division of the mature miHeps had been greatly decreased due to the effect of the maturation medium, there was no particular change in the number of Ki-67⁺ cells although treated with the conditioned media of hASCs cultured two- or three-dimensionally. However, the number of albumin⁺ cells was greatly increased at a significant level when treated with the conditioned media of hASCs cultured two- or three-dimensionally. These results imply that factors capable of regulating miHeps division and maturation are included in secretome of hASCs, particularly, secretome of hASCs cultured three-dimensionally, and in order to form a hASC-miHep organoid having a more matured hepatocyte-specific phenotype, maturity of miHeps co-cultured with hASCs under three-dimensional conditions may act as an important factor.

Example 4. Effect of Secretome on hDF and hBMSC

To examine whether the effect of modulating hepatic functions of miHep by secretome of hASCs may be also observed in secretome in another mesenchymal stem cells, conditioned media obtained from human dermal fibroblasts (hDFs) and human bone marrow-derived mesenchymal stem cells (hBMSCs) were used to perform the same experiment as in Example 4.

Figure 6A:
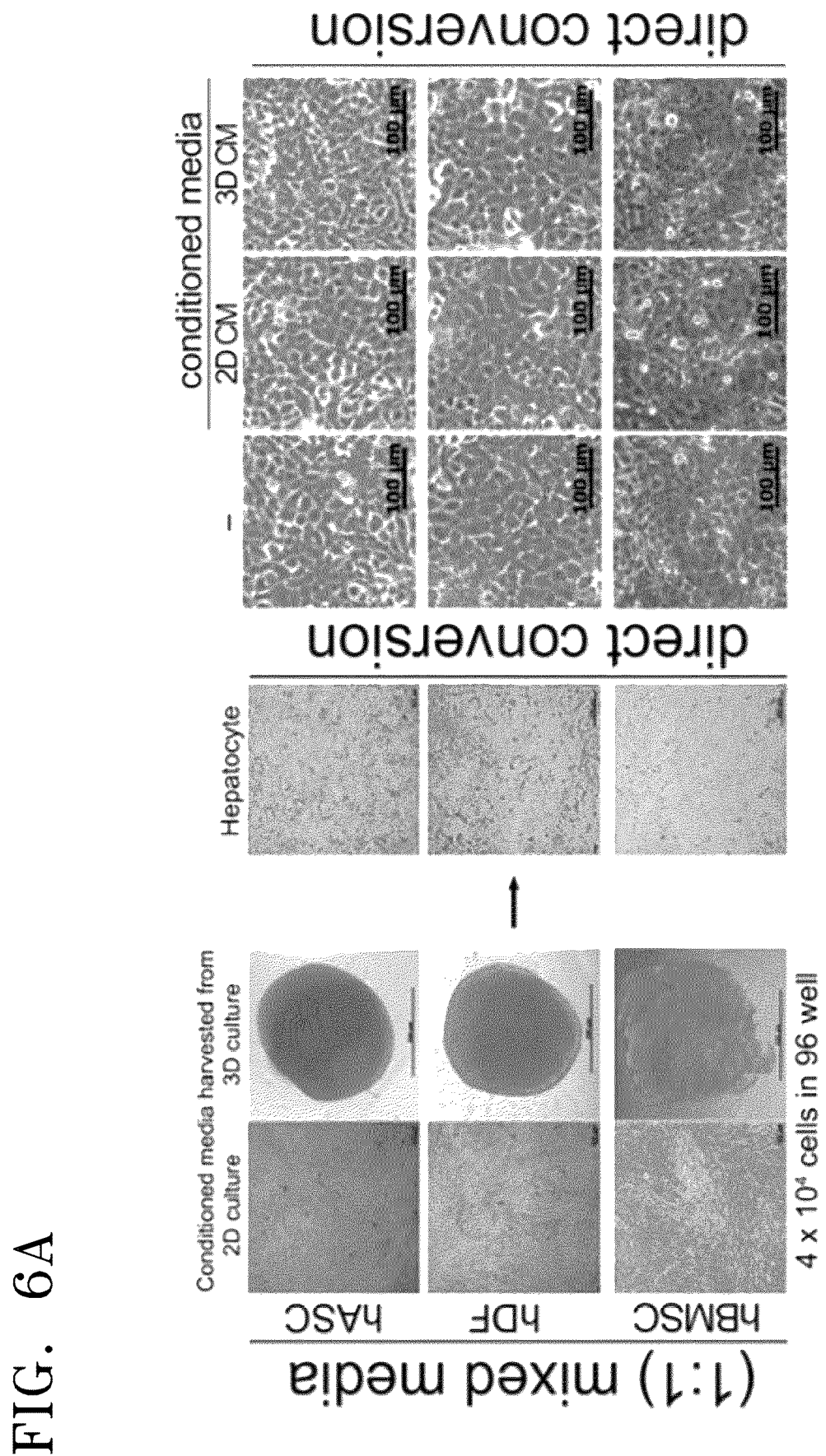
FIG. 6A shows photographs showing the result of treating two-dimensionally cultured hDFs and hBMSCs with conditioned media.
Figure 6B:
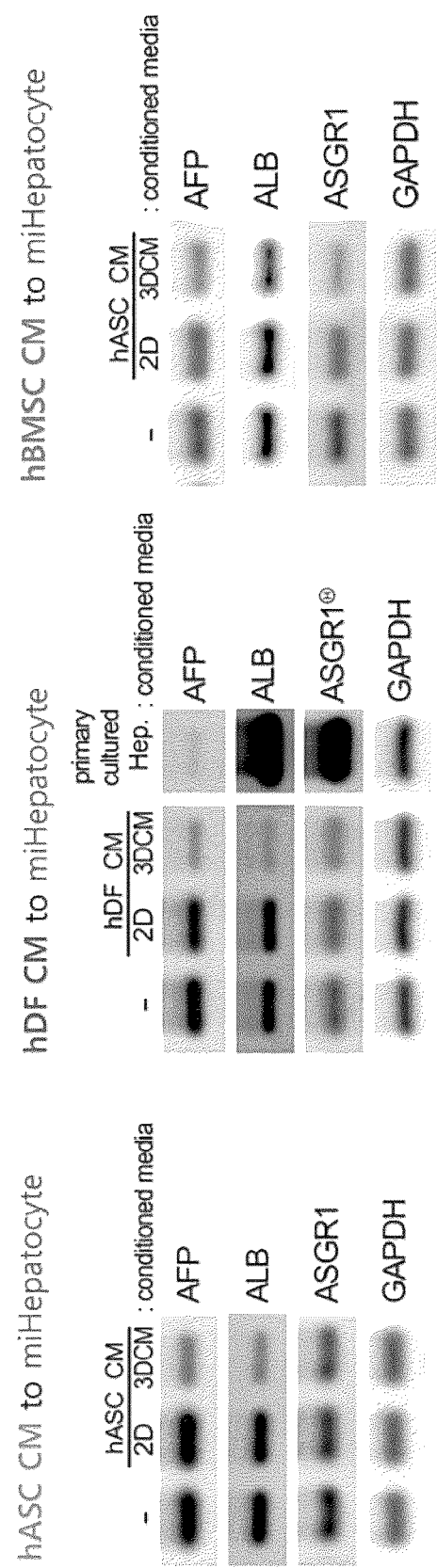
FIG. 6B shows the result of examining hepatocyte-specific gene expression of the hDFs and hBMSCs.

FIG. 6A shows photographs showing the results of treating two-dimensionally cultured hDFs and hBMSCs with conditioned medium, and FIG. 6B shows the result of examining hepatocyte-specific gene expression of hDFs and hBMSCs.

As shown in FIG. 6A, the conditioned media obtained by two- and three-dimensional culture of the respective cells caused no particular change in the morphology when treated to mature and immature miHeps, as in the results of hASCs. However, as shown in FIG. 6D, when expression of hepatocyte-specific genes was examined by RT-PCR, hepatic functions of immature miHeps were gradually reduced by treatment of two- or three-dimensional hDF and hBMSC culture media, like the treatment of hASC culture medium, although there was a difference in the degree depending on the kind of cell. These results imply that factors capable of ambivalently modulating the hepatocyte-specific gene expression according to the maturity of miHeps exist in the secretome of another mesenchymal stem cells such as hDFs and hBMSCs as well as in the secretome of hASCs. To examine factors actually secreted by hASC, hDF, and hBMSC, the respective cells were cultured two- and three-dimensionally, and the cell lysates were used to perform a growth factor array. As a result, when all the three kinds of cells were cultured under two- or three-dimensional conditions, expression of various growth factors capable of promoting cell division and differentiation such as EGF, FGF, HGF, IGF, PDGF, TGF and VEGF was promoted. These results suggest that the maturity of hepatic progenitor may be actually a very important factor in the formation of a liver mimetic tissue having a high level of hepatic function, and in order to elicit higher hepatic functions from the formed liver mimetic tissue, secretome secreted by surrounding environment constituting the liver tissue including the mature hepatocytes, in particular, peripheral cells such as mesenchymal stem cells may play an important role.

Example 5. Formation of hASC-hCdH Organoids

To form hASC-hCdH organoids by three-dimensional cell culture, three-dimensional cell spheroids (hASC-hCdH organoids) were prepared from hCdHeps and hASCs obtained in Example 2-1. Organoids were prepared by co-culturing hCdHeps and hASCs on a non-tissue culture matrix (poly-styrene-maltose-binding protein-basic fibroblast growth factor 2(PS-MBP-FGF2) matrix). In detail, hASCs obtained in Example 2-1 were seeded on the matrix at a density of $0.67 \times 10^5$ cells/cm², and then incubated for 2 hours. Thereafter, hCdHeps were additionally seeded at a density of $0.33 \times 10^5$ cells/cm², and then incubated for 2 days.

Example 6. Formation of hASC-hCdH Organoids Using Artificial Ligand of Hepatocyte-Specific Receptor To compensate for the decrease in the yield of organoid formation as the proportion of hCdHeps cells in all the cells used for organoid formation is increased in Example 5, an artificial ligand poly[N-p-vinylvenzyl-O-β-galactopyranosyl-(1->4)-d-gluconamide](PVLA) of a hepatocyte-specific protein ASGP-R was further used to prepare three-dimensional cell spheroids (hASC-hCdH organoids) from hCdHeps and hASCs obtained in Example 2-1. PVLA was further immobilized at a concentration of 10 μg/ml to 20 μg/ml on a non-tissue culture matrix (poly-styrene-maltose-binding protein-basic fibroblast growth factor 2(PS-MBP-FGF2) matrix) on the surface of culture plate, and then organoids were formed by co-culturing hCdHeps with hASCs. In detail, hASCs obtained in Example 2-1 were seeded on the matrix at a density of $0.67 \times 10^5$ cells/cm$^2$, and then incubated for 2 hours. Thereafter, hCdHeps were additionally seeded at a density of $0.33 \times 10^5$ cells/cm$^2$, and then incubated for 2 days.

Experimental Example

Characterization of Organoid

Figure 7A:
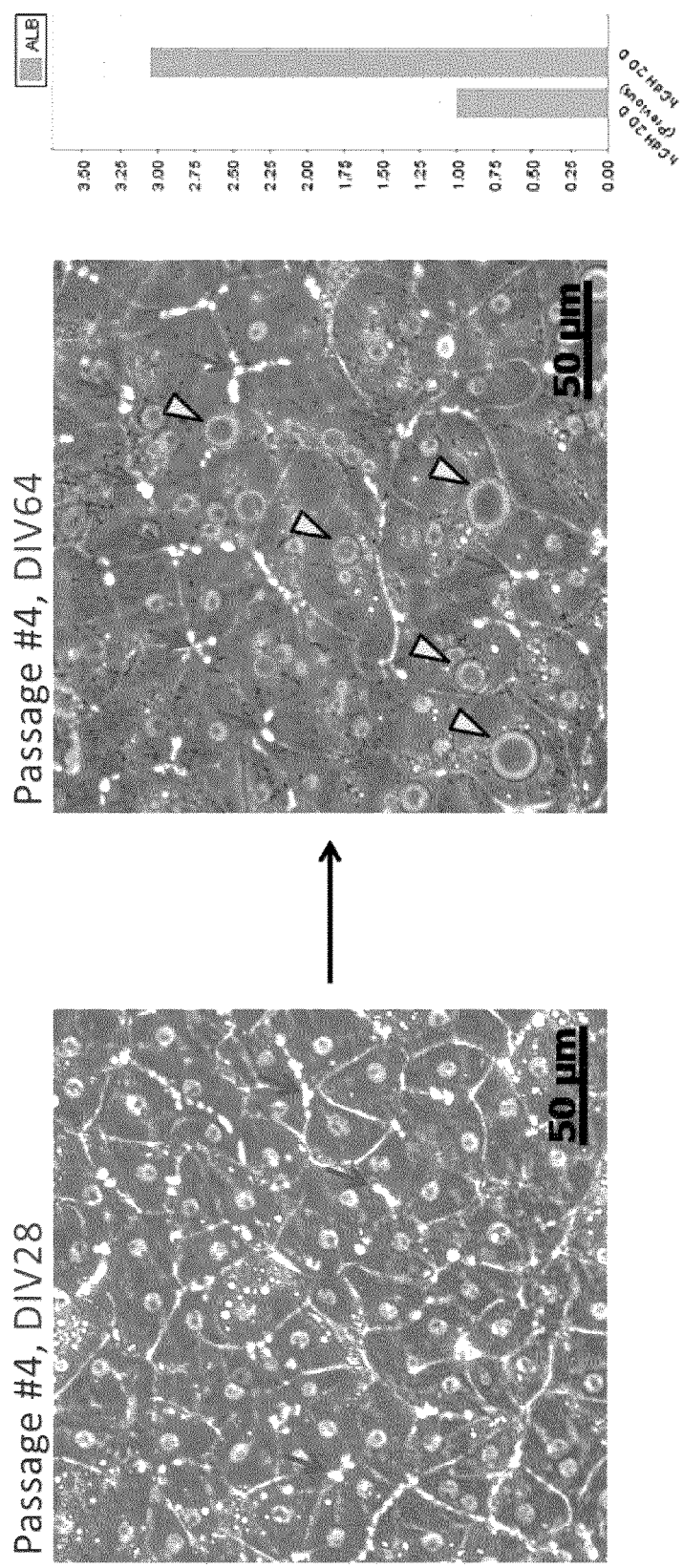
FIG. 7A shows photographs showing the morphological change of hCdHep2 under two-dimensional culture, wherein maturation of hCdHeps during culture for 28 days to 64 days is shown, red arrows indicate bile canaliculi, and yellow arrows indicate glycogenated nuclei, and the graph shows the RT-PCR result of examining increased expression of a hepatocyte-specific factor ALB to further examine maturation of hepatocytes during culture.
Figure 7B:
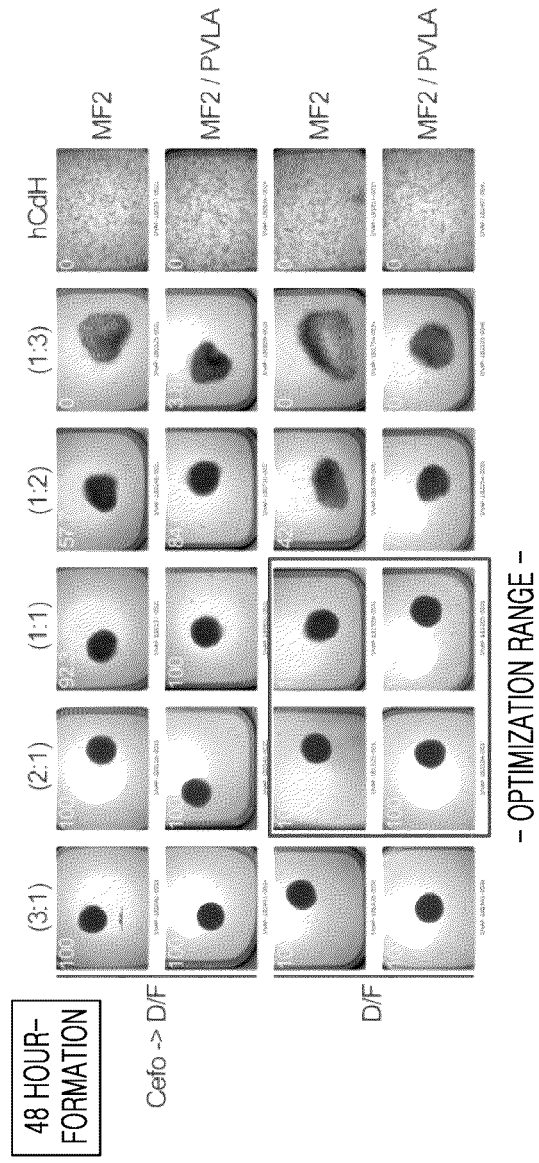
FIG. 7B shows morphology and yield (yellow figures) of cell spheroids formed for 48 hours by varying media (hASC growth medium; Cefo, hCdHeps growth medium; D/F), a ratio of hASCs co-cultured with hCdHeps (3:1 to 1:3, or hCdHeps alone), and coating conditions (single coating of MF2 or co-coating of MF2 and PVLA) during a formation process of cell spheroids.
Figure 7C:
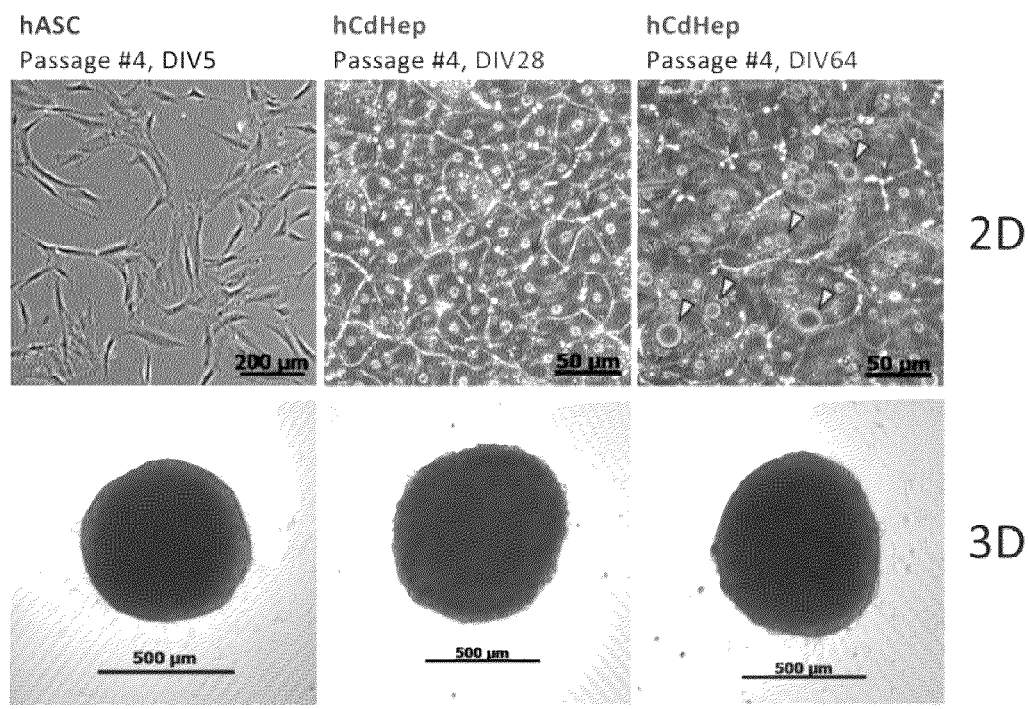
FIG. 7C shows morphology (3D) of cell spheroids formed at 48 hours when hASCs were cultured alone or co-cultured with hCdHeps at a maturation stage of 28 days or 64 days under optimized conditions for cell spheroid formation (confirmed as in FIG. 7B; D/F, 2:1, MF2/PVLA), and morphology (2D) of cells used in the formation of the cell spheroids.

For morphological optimization of the three-dimensional cell spheroid formed in Example 5, cells in which morphological features of mature hepatocytes (FIG. 7A, image) and increased expression of albumin (ALB) as a representative hepatocyte marker (FIG. 7A, right graph) were confirmed were obtained, and then the corresponding cells were seeded together with hASCs, and 48 hours later, morphologies of formed cell spheroids were photographed using an optical microscope (FIG. 7B). In detail, conditions under which cells uniformly aggregate as one cluster were examined by varying a cell ratio of hASC:hCdH, conditions of culture medium, and additional PVLA coating on the non-tissue culture matrix (poly-styrene-maltose-binding protein-basic fibroblast growth factor 2(PS-MBP-FGF2) matrix), and the medium and coating conditions under which the cells may maintain higher hepatic functions were considered to determine an optimized range (FIG. 7B; red box). To examine the effect of maturity of hCdHs co-cultured with hASCs on the formation of cell spheroid by using the cell ratio (2:1), medium (DMEM/F12 for hCdH), and coating conditions (MF2/PVLA) thus determined, morphologies of cell spheroids which were prepared using two kinds of hCdH cells at different maturation stages were observed using an optical microscope (FIG. 7C). Further, to examine whether the prepared hASC-hCdH organoids have hepatic functions, expression of representative hepatocyte markers (ALB, HNF1a, CYP1a2, and ASGR1) was examined by real-time polymerase chain reaction.

Figure 7D:
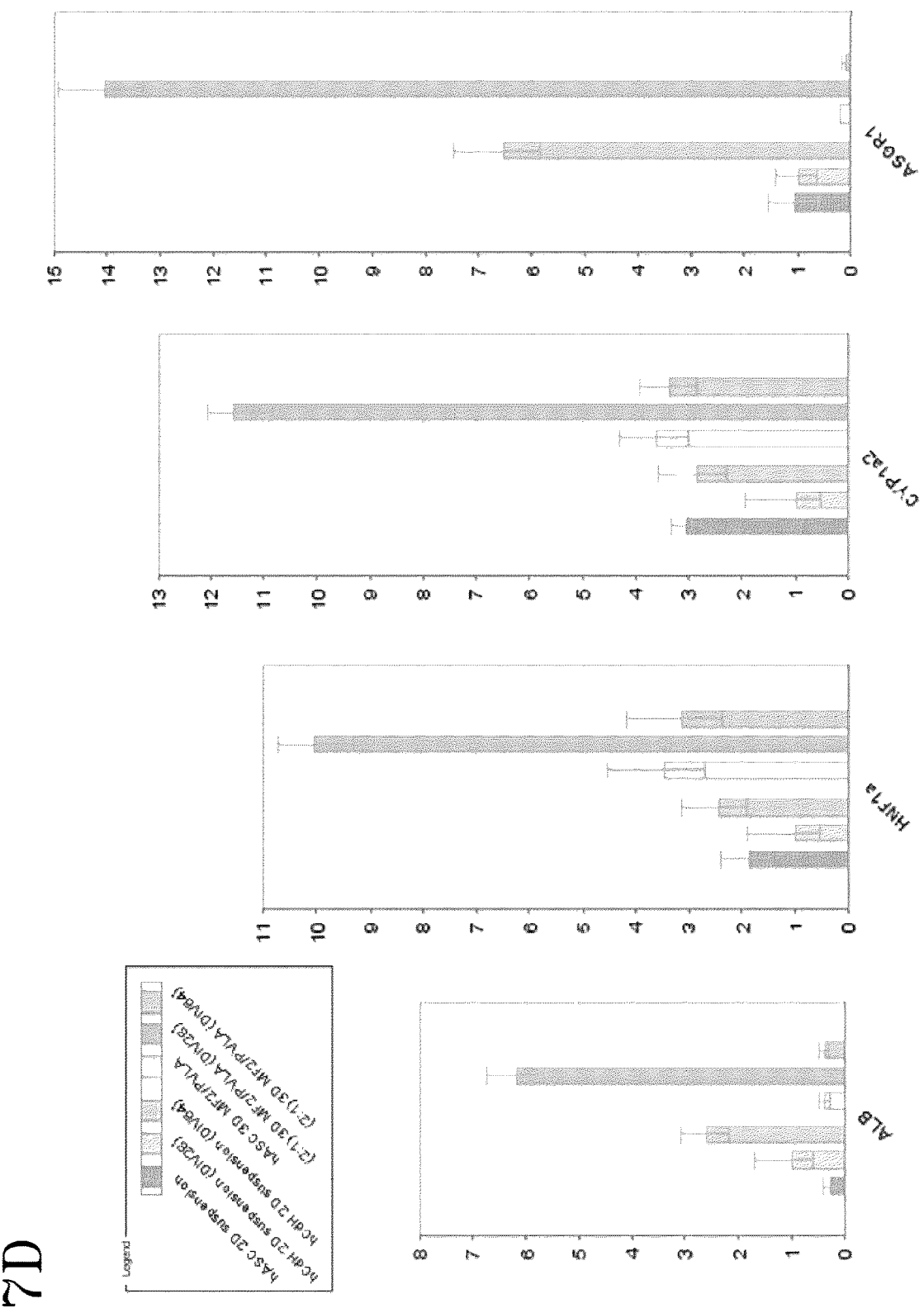
FIG. 7D shows the result of real-time PCR which was performed using two-dimensional cells (hASCs, hCdHeps at a maturation stage of 28 days and hCdHeps at a maturation stage of 64 days) and three-dimensional cell spheroids (hASCs alone, co-culture of hASCs with hCdHeps at a maturation stage of 28 days or 64 days) shown in FIG. 7C to evaluate hepatic functions of the prepared cell spheroids.
Figure 7E:
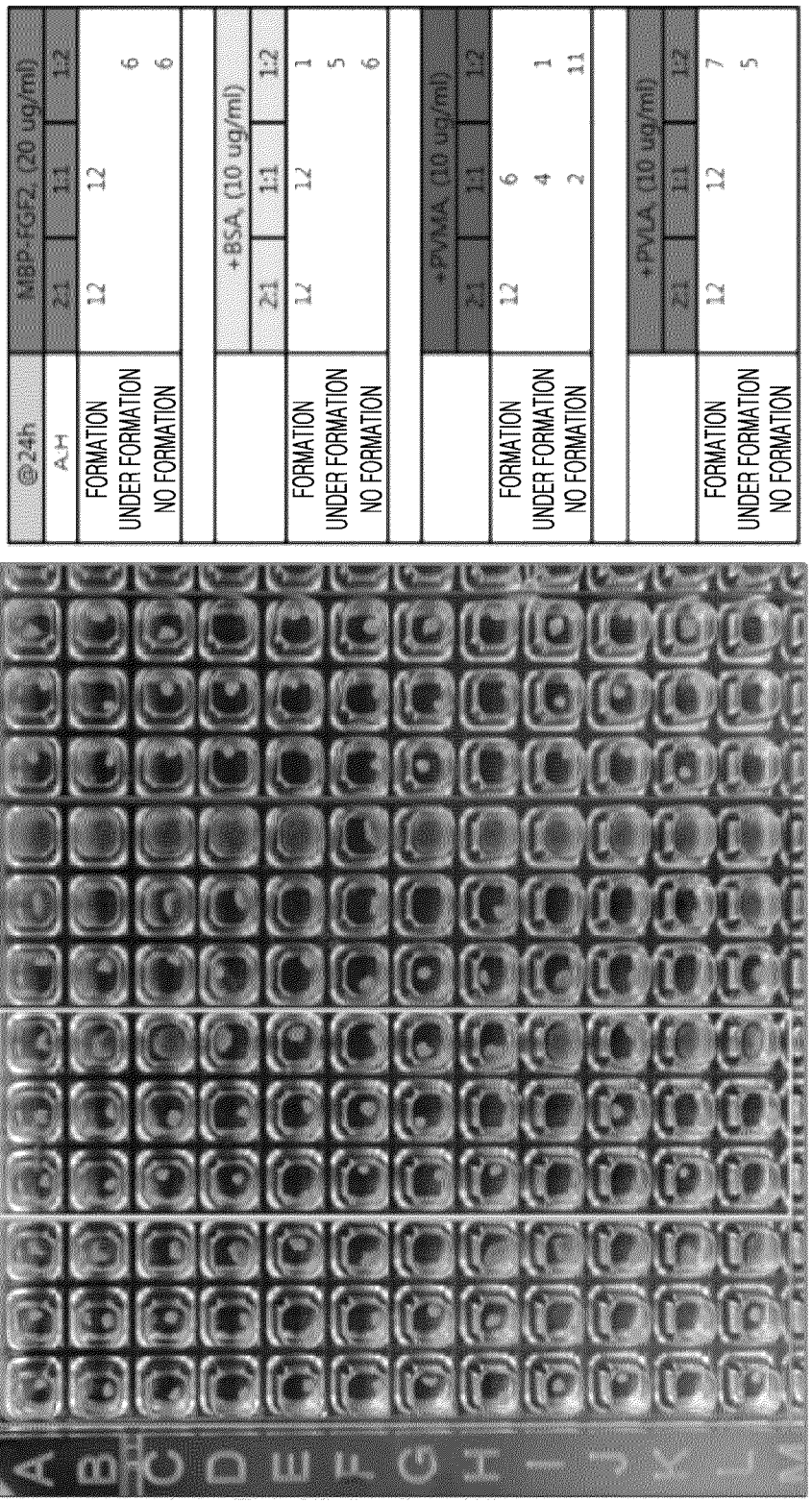
FIG. 7E shows morphologies (left image) and formation yields (right table) of cell spheroids which were formed while varying a ratio of hASCs and hCdHeps at 2:1, 1:1, and 1:2 under single coating of MBP-FGF2 versus co-coating of an artificial ligand PVLA with MBP-FGF2.

As a result, as shown in FIG. 7D, the hepatocyte-specific gene expression (ALB, HNF1a, CYP1a2, and ASGR1) of the three-dimensional cell spheroid (green) co-cultured three-dimensionally was increased 6 to 14 times, as compared with that of mature hCdHeps (cyan) cultured two-dimensionally for 28 days. That is, when cell spheroids are formed using hCdH at a maturation stage of 28 days, hepatic functions may be greatly improved.

Enhancement of Organoid Formation by PVLA Coating

To compensate for the decrease in the yield of cell spheroid formation when hepatic progenitors are co-cultured with hASCs on a non-tissue culture matrix (poly-styrene-maltose-binding protein-basic fibroblast growth factor 2(PS-MBP-FGF2) matrix), a hepatocyte-specific artificial ligand (PVLA), which specifically binds to ASGP receptors expressed on the surface of hepatocytes to weaken a binding force between the hepatocytes and a poly-styrene culture plate, was coated together with MBP-FGF2 onto the surface of the poly-styrene culture plate. In detail, as a control group of amphipathic PVLA molecule having a binding ability to both the surface of the poly-styrene culture plate and ASGP receptor which is a hepatocyte membrane protein, a similar molecule PVMA having a binding ability to the poly-styrene surface, like PVLA, but having no a binding ability to ASGP receptor was used. To examine whether hydrophobicity of the poly-styrene culture plate due to non-specific coating affects the change of yield, BSA was used.

As a result, as shown in FIG. 7A, when co-coating of MBP-FGF2 and PVLA was performed at a cell ratio of hASC:hCdH(1:2) in which the ratio of hepatic progenitors began to inhibit cell spheroid formation, frequency of cell spheroid formation was increased, as compared with single MBP-FGF2(MF2) coating or MF2+BSA and MF2+PVMA (amphipathic PVLA-like molecule having no binding ability to ASGP receptor). In detail, when the co-coating of MBP-FGF2 and PVLA was compared with single MBP-FGF2 coating, a ratio of no spheroid formation was reduced from 6 to 0 out of total 12 and a ratio of spheroid formation was greatly increased from 0 to 7 at the hASC:hCdHeps ratio of 1:2. Further, it was confirmed that the cell spheroids formed under co-coating of MBP-FGF2 and PVLA maintained a more stable spherical form than those formed under single coating of MBP-FGF2. In other words, the cell spheroids formed at a co-culture ratio of 2:1 and 1:1 showed a denser and more stable morphology than those formed under single coating of MBP-FGF2.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of preparing a three-dimensional cell co-spheroid, the method comprising:
    introducing Foxa3 factor and hepatocyte nuclear factor 4 alpha (HNFα) to hepatic progenitors, and culturing the hepatic progenitors in a hepatocyte maturation medium for 7 days to 28 days, thereby differentiating the hepatic progenitors into hepatic differentiated cells and thereby increasing expression of hepatocyte-specific gene HNFα, alpha-fetoprotein (AFP), albumin (ALB), asialoglycoprotein Receptor 1 (ASGR1), and Cytochromes P450 (CYP450);
    adherent-culturing adipose-derived mesenchymal stem cells in a culture plate having a hydrophobic surface, wherein the culture plate is coated with maltose-binding protein-fibroblast growth factor 2 (MBP-FGF2) and poly-(N-p-vinylbenzyl-O-β-D-galactopyranosyl-[1-4]-D-gluconamide (PVLA) and the culture plate is two-dimensional or the hydrophobic surface is flat; and
    seeding the hepatic differentiated cells into the culture plate having a hydrophobic surface, thereby co-culturing the adherent-culturing adipose-derived mesenchymal stem cells with the hepatic differentiated cells; and
    forming the three-dimensional cell co-spheroid by detaching the adipose-derived mesenchymal stem cells and the hepatic differentiated cells from the culture plate.

2. The method of claim 1, wherein the cell co-spheroid has a diameter of 300 μm and 2000 μm.

3. The method of claim 1, wherein the adipose-derived mesenchymal stem cells and the hepatic differentiated cells are mixed at a ratio of 1:5 to 5:1.

4. The method of claim 1, wherein the co-culture is performed for 20 hours to 60 hours.

5. The method of claim 1, wherein the adipose-derived mesenchymal stem cells are human adipose-derived mesenchymal stem cells.

6. A three-dimensional cell co-spheroid prepared by the method of claim 1.

7. A method of preventing or treating liver disease, the method comprising administering to a subject a cellular therapeutic agent comprising three-dimensional cell co-spheroids prepared by the method of claim 1.

8. The method of claim 7, wherein the cellular therapeutic agent comprises a culture medium comprising the cell co-spheroids.

9. The method of claim 8, wherein the culture medium is mixed at a ratio of 100 μl to 500 μl per 1 unit of the cell co-spheroids.

10. The method of claim 8, wherein the culture medium is obtained from a medium where the cell co-spheroids are three-dimensionally cultured.

11. The method of claim 8, wherein the culture medium comprises a factor promoting hepatocyte division and maturation.

12. The method of claim 7, wherein the liver disease is selected from the group consisting of hepatitis, hepatotoxicity, cholestasis, fatty liver, cirrhosis, liver ischemia, alcoholic liver disease, hepatic abscess, hepatic coma, hepatatrophia, and hepatic cancer.

* * * * *